United States Patent
Kennedy et al.

(10) Patent No.: US 9,421,053 B2
(45) Date of Patent: Aug. 23, 2016

(54) IMPLANT FIXATION ASSEMBLIES HAVING A SCREW AND C-SHAPED FIXATION COLLAR

(71) Applicant: Titan Spine, LLC, Mequon, WI (US)

(72) Inventors: Eric Kennedy, Mequon, WI (US); Chad J. Patterson, Port Washington, WI (US); Carmie A. Thompson, III, Milwaukee, WI (US)

(73) Assignee: Titan Spine, LLC, Mequon, WI (US)

( * ) Notice: Subject to any disclaimer, the term of this patent is extended or adjusted under 35 U.S.C. 154(b) by 295 days.

(21) Appl. No.: 14/272,557

(22) Filed: May 8, 2014

(65) Prior Publication Data

US 2015/0320466 A1    Nov. 12, 2015

(51) Int. Cl.
| | |
|---|---|
| *A61B 17/86* | (2006.01) |
| *A61B 17/88* | (2006.01) |
| *A61B 17/80* | (2006.01) |
| *A61F 2/44* | (2006.01) |
| *A61B 17/70* | (2006.01) |

(52) U.S. Cl.
CPC ....... *A61B 17/8605* (2013.01); *A61B 17/7059* (2013.01); *A61B 17/8033* (2013.01); *A61B 17/8047* (2013.01); *A61B 17/8875* (2013.01); *A61F 2/4455* (2013.01)

(58) Field of Classification Search
CPC .......... A61B 17/8047; A61B 17/8605; A61B 17/8033; A61F 2/4455
See application file for complete search history.

(56) References Cited

U.S. PATENT DOCUMENTS

| | | |
|---|---|---|
| 5,364,399 A | 11/1994 | Lowery et al. |
| 5,797,912 A | 8/1998 | Runciman et al. |
| 6,241,731 B1 | 6/2001 | Fiz |
| 6,575,975 B2 | 6/2003 | Brace et al. |
| 6,602,255 B1 | 8/2003 | Campbell et al. |
| 6,623,485 B2 | 9/2003 | Doubler et al. |
| 6,695,846 B2 | 2/2004 | Richelsoph et al. |
| 7,309,340 B2 | 12/2007 | Fallin et al. |
| 7,758,620 B2 | 7/2010 | Porcher |
| 7,887,547 B2 | 2/2011 | Campbell et al. |
| 7,914,561 B2 * | 3/2011 | Konieczynski .... A61B 17/8042 606/280 |
| 7,931,681 B2 | 4/2011 | Carls et al. |
| 7,942,913 B2 * | 5/2011 | Ziolo ................. A61B 17/8047 606/287 |

(Continued)

FOREIGN PATENT DOCUMENTS

| | | |
|---|---|---|
| FR | 2861980 | 5/2005 |
| WO | 2005053550 | 6/2005 |
| WO | 2008118599 | 10/2008 |

OTHER PUBLICATIONS

International Search Report and Written Opinion issued in related application PCT/US15/29816 dated Jul. 20, 2015.

*Primary Examiner* — Andrew Yang
(74) *Attorney, Agent, or Firm* — Stradley Ronon Stevens & Young, LLP

(57) ABSTRACT

A system for anchoring implants to bones comprises a screw and fixation collar that when connected together inhibit axial movement of the screw and that when connected to an implant with a compatibly shaped aperture inhibit the screw's ability to back out from the bone and back out from the implant. The fixation collar includes a substantially C-shaped configuration partially surrounding a void, with first and second ends defining a gap that is slightly narrower in width than the diameter of the screw and being partially flexible to allow compression and expansion of the fixation collar to snap fit the collar around the screw.

21 Claims, 21 Drawing Sheets

(56) References Cited

U.S. PATENT DOCUMENTS

| | | |
|---|---|---|
| 7,972,366 B2 | 7/2011 | Richelsoph et al. |
| 8,118,849 B2 | 2/2012 | Wahl et al. |
| 8,172,885 B2 | 5/2012 | Songer et al. |
| 8,282,675 B2 | 10/2012 | Maguire et al. |
| 8,287,550 B2 | 10/2012 | Campbell et al. |
| 8,287,575 B2 * | 10/2012 | Murner ............ 606/287 |
| 8,328,856 B1 | 12/2012 | Donahoe et al. |
| 8,361,126 B2 | 1/2013 | Perrow et al. |
| 8,388,666 B2 | 3/2013 | Castaneda et al. |
| 8,529,609 B2 | 9/2013 | Helgerson et al. |
| 8,585,743 B2 | 11/2013 | Ampuero et al. |
| 8,632,575 B2 | 1/2014 | Weiman et al. |
| 8,702,762 B2 | 4/2014 | Jacene et al. |
| 8,721,694 B2 | 5/2014 | Patterson et al. |
| 8,734,494 B2 | 5/2014 | Simon et al. |
| 9,198,769 B2 * | 12/2015 | Perrow ............ A61B 17/8042 |
| 2004/0127900 A1 | 7/2004 | Konieczynski et al. |
| 2008/0183293 A1 | 7/2008 | Parry et al. |
| 2008/0275510 A1 | 11/2008 | Schonhardt et al. |
| 2011/0166656 A1 | 7/2011 | Thalgott et al. |
| 2011/0166657 A1 | 7/2011 | Thalgott et al. |
| 2011/0313466 A1 | 12/2011 | Butler et al. |
| 2012/0095514 A1 | 4/2012 | Lombardo et al. |
| 2012/0136396 A1 | 5/2012 | Baker et al. |
| 2013/0018427 A1 | 1/2013 | Pham et al. |
| 2013/0053967 A1 | 2/2013 | Sournac et al. |
| 2013/0310881 A1 | 11/2013 | Klein |
| 2014/0081269 A1 | 3/2014 | Biedermann |

\* cited by examiner

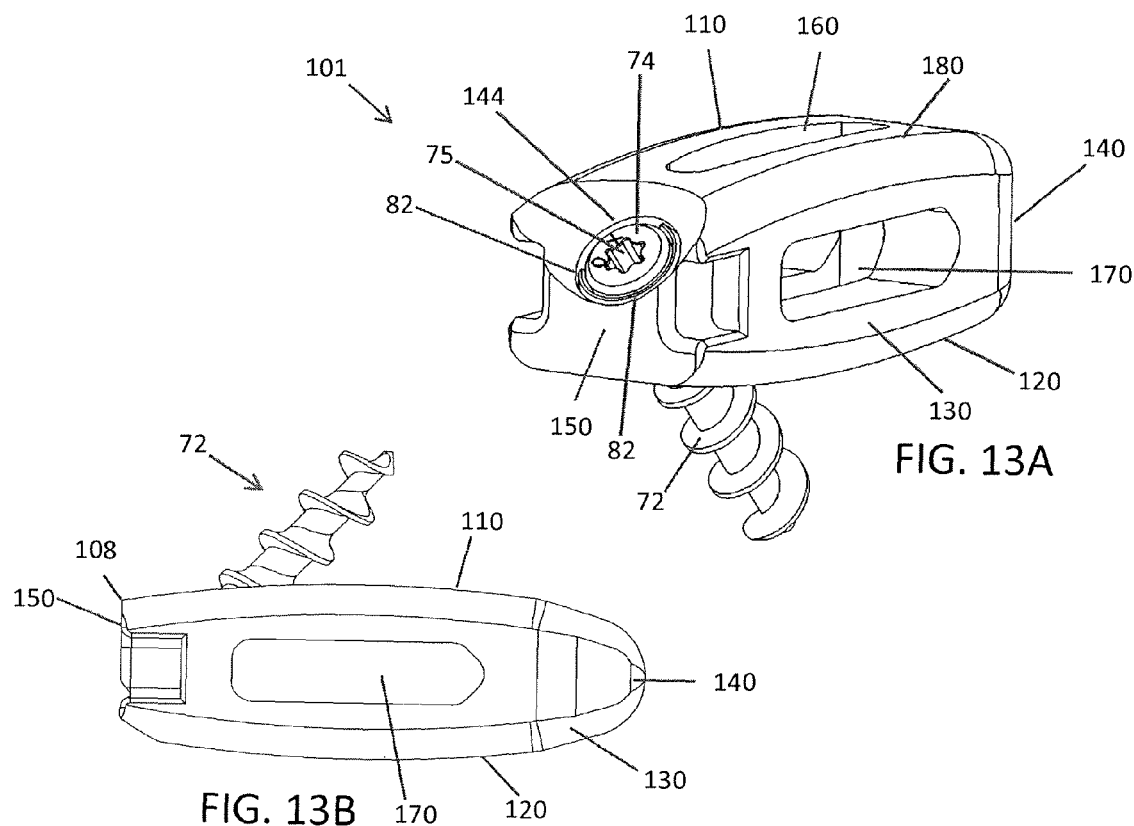
FIG. 13A
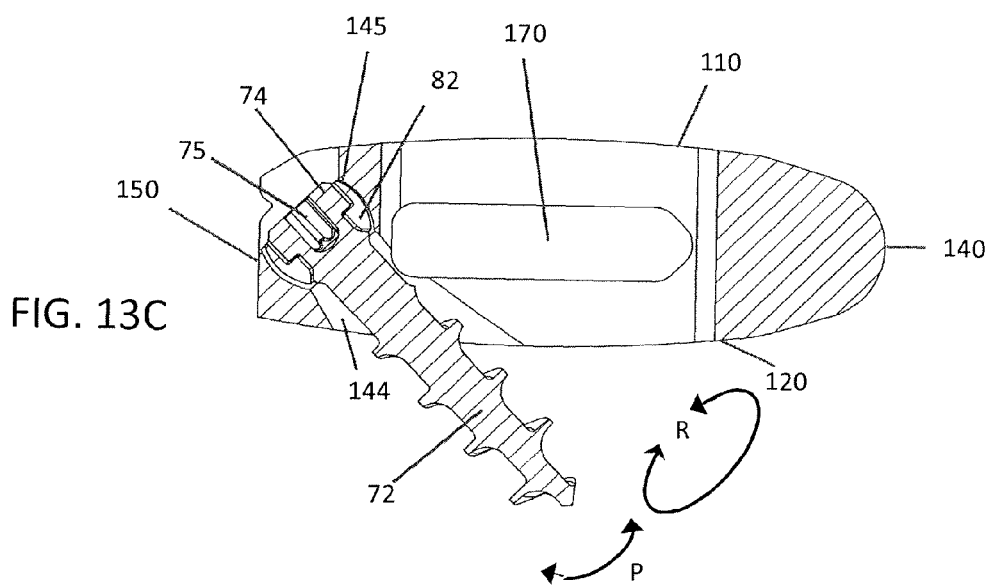
FIG. 13B
FIG. 13C

Ra = Average (1, 4, 6, 8, 5, 2, 1, 4, 1, 2, 1, 4, 7, 4, 1, 2, 5, 8, 2, 1, 4, 1, 1)

Ra = 3.26

$Rpm = average(Rp1, Rp2, Rp3, ...)$
$Rvm = average(Rv1, Rv2, Rv3, ...)$
$RzDIN = Rtm = average(Rt1, Rt2, Rt3, ...)$

IMPLANT FIXATION ASSEMBLIES HAVING A SCREW AND C-SHAPED FIXATION COLLAR

FIELD OF THE INVENTION

The invention relates generally to interbody spinal implants that employ bone screws to secure the implant to adjacent vertebrae, with the bone screws flexibly secured within the implants by way of a C-shaped fixation collar. More particularly, the invention relates to structural features of the fixation collar that allow the collar and screw to be assembled together without damage to the collar, yet still providing for an appropriate level of maneuverability of the screw within the collar. The structural features include partially flexible end regions and notches at the end regions of collar sidewalls.

BACKGROUND OF THE INVENTION

Various publications, including patents, published applications, technical articles and scholarly articles are cited throughout the specification. Each of these cited publications is incorporated by reference, in its entirety and for all purposes, in this document.

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Spinal fusion procedures can be achieved using a posterior or an anterior approach, for example. Anterior interbody fusion procedures generally have the advantages of reduced operative times and reduced blood loss. Further, anterior procedures do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

Some of the common problems with spinal implants include movement or expulsion of the implant once inserted between adjacent vertebrae. In particular, when the flexible tissue (the annulus) connecting the disks is severed in the surgical procedure additional vertical and lateral instability in the joint is induced. In order to reduce implant movement or expulsion from between the vertebral bodies, spinal implants may be affixed to adjacent vertebrae, for example, using additional fixation elements, such as screws. The use of additional fixation outside of the joint space, for example, by using screws and plates, screws and rods, or screws alone can limit the amount of displacement that occurs as the vertebra move away from one another reducing movement and activity. Unfortunately, screws can loosen, back out, and even break over time.

A number of screw retention or secondary screw fixation devices are available to try to combat the problem of back out. For example, a screw locking plate and fastener assembly may be placed over the heads of the screws or a snap may be embedded into the implant body. Typical screw retention devices rigidly fix the screws within the device. This rigidity does not allow for movement of the screws, however, and can result in increased loading in the joint space. In other words, the loading can create pressure points where the screws are located and can produce undesired bone remodeling at those locations. Similarly, implants having aggressive teeth or ridges can remodel the bone around these sharp features providing instability and movement in the joint assembly. Rigid fixation, increased loading and pressure points, and movement and instability of the implant can result in mechanical failure of the screws. Mechanical failure of the screws and associated pieces of the screw retention devices (e.g., screw locking plate, etc.) places the patient at risk for unsecured screws in the vertebral disk space.

One attempt at addressing the screw back-out problem is provided in U.S. Pat. No. 6,241,731, which describes a plate and screw assembly for fixing bones wherein the screw includes a retainer fitted about the head of the screw for limiting axial movement of the screw after installation with the plate. The plate has at least one orifice which defines a cavity for receiving the screw head and retainer therein such that there should be free pivotal movement, but limited axial movement, of the screw to prevent the screw from moving out of the orifice of the plate. Rather than having a complete annular ring shape, the retainer has a "C" shape with a uniformly-sized, axially-oriented slot which enables the retainer to slightly yield to compression forces or slightly flex in response to expansion forces, which facilitates insertion and retention of the coupled screw head and retainer in the orifice of the plate.

Construction and use of the plate and screw assembly of U.S. Pat. No. 6,241,731 has been found to be impracticable. For example, it was found that the retainer could not be made with an effectively-sized slot that could at the same time allow the retainer to be placed around the screw in a manner that prevented axial movement of the screw and support load forces. A proper balance between strength and flexibility could not be achieved with this plate and screw design. When the retainer was constructed of material strong enough to secure the implant and support the expected load forces, the width of the slot required to allow coupling with the screw head without damage to the retainer body was too wide to securely and pivotably retain the screw head therein. Conversely, when the width of the slot was made narrow enough to ensure that the screw head was pivotably secured in the retainer, the retainer body cracked or broke when the retainer and screw head were brought together, i.e., the retainer was not strong and could not support assembly forces, let alone load forces.

Thus, a need remains for a screw fixation device that can secure a screw in an implant device without the risk of back out or fracture of the screw, but does not create any of the problems mentioned above for traditional screw retention devices. It is desirable to have a screw fixation device that at the same time minimizes or prevents axial movement of the screw, and allows full pivotal movement of the screw relative to the implant device after surgical implantation, and furthermore, the fixation device must be capable of being coupled to the screw without structural damage or failure to the fixation device.

SUMMARY OF THE INVENTION

The invention features assemblies for enhancing the fixation of an implant to adjacent bone. The assemblies include a screw and fixation collar. The screw comprises a head, a shoulder beneath the head, a groove between the head and shoulder, and a threaded shaft beneath the shoulder. The fixation collar is preferably substantially C-shaped, and comprises a sidewall at least partially surrounding a void that is substantially in the center of the collar and extends along an axis that is parallel to the vertical axis of the fixation collar. The sidewall comprises a recessed top portion that forms a ridge on which the bottom of the head sits when the screw is inside of the void, a bottom portion that engages the groove when the screw is inside of the void, end regions that are partially flexible along an axis that is perpendicular to the vertical axis of the fixation collar, and a first end and second end defining a gap in communication with the void. Each of the first and ends comprise a first notch above the ridge and a second notch below the ridge. The gap has a width slightly narrower than the inner diameter of the groove. The void has a diameter narrower than the outer diameter of the shoulder such that the screw may not be moved axially completely through the fixation collar. The sidewall may comprise a convex outer surface configured to engage an aperture having concave sidewalls in an implant in a way that inhibits axial movement of the screw and collar assembly out from the aperture once engaged, but allows limited pivotal and rotational movement of the screw and collar assembly about the aperture. In some aspects, the groove and bottom portion comprise compatibly shaped undercuts. The void may have a diameter narrower than the outer diameter of the screw threads.

In highly preferred aspects, the first notch is radiused in a direction away from the gap. The second notch may also be radiused in a direction away from the gap. The first notch on each end generally widens the gap above the ridge. The width of the gap above the ridge is preferably about 10% to about 60% greater than the width of the gap below the ridge. The first notch on each end may define a ledge on the ridge. The ledge preferably comprises blunt and radiused edges.

The screw or the fixation collar may comprise a plastic, polymeric, or non-metal composite material. The screw or the fixation collar may comprise a metal such a titanium. At least a portion of the screw, preferably the portion that is inserted into bone, may comprise a roughened surface topography comprising macro-, micro-, and nano-scale structures capable of facilitating bone growth. The screw threads may comprise the roughened surface topography.

The invention also features systems for anchoring an implant to adjacent bone. The systems comprise an implant, a screw, and a fixation collar, which preferably has a sidewall comprising a convex outer surface. The implant may be any implant. In some preferred aspects, the implant is an intervertebral implant. The implant comprises one or more apertures extending through the implant body such that the screw may pass through the implant and into adjacent bone. The aperture comprise an opening having a diameter narrower than the widest point of the convex outer surface of the fixation collar and a concave inner surface that engages the sidewall of the fixation collar when the fixation collar is inside of the aperture. The one or more apertures may further comprise one or more flutings along the periphery of the aperture. In addition to or instead of the flutings, the implant may further comprise one or more slots in communication with the aperture into which a tool may be inserted to dislodge the fixation collar from the aperture. At least a portion of the surface(s) of the implant that contact bone may comprise a roughened surface topography comprising macro-, micro-, and nano-scale structures capable of facilitating bone growth.

BRIEF DESCRIPTION OF THE DRAWINGS

The invention is best understood from the following detailed description when read in connection with the accompanying drawings, in which like reference numbers refer to like elements throughout the various figures. It is emphasized that, according to common practice, the various features of the drawing are not to scale. On the contrary, the dimensions of the various features are arbitrarily expanded or reduced for clarity. Included in the drawings are the following figures in which:

FIG. 13A shows a perspective view of an implant, screw and fixation collar assembly;

FIG. 13B shows a side view of an implant, screw and fixation collar assembly;

FIG. 13C shows a cross-sectional view of an implant, screw and fixation collar assembly;

DETAILED DESCRIPTION OF THE INVENTION

Various terms relating to aspects of the present disclosure are used throughout the specification and claims. Such terms are to be given their ordinary meaning in the art, unless otherwise indicated. Other specifically defined terms are to be construed in a manner consistent with the definition provided in this document.

As used throughout, the singular forms "a," "an," and "the" include plural referents unless expressly stated otherwise.

The terms subject and patient are used interchangeably. A patient may be any animal, including mammals such as companion animals, laboratory animals, and non-human primates. Human beings are preferred.

The invention provides for spinal implants having screw assemblies including a fixation collar that prevents the screw from backing out of the implant, once inserted. The fixation collar is sized and shaped in a manner such that the screw is pivotally movable about the collar, but is prevented from moving axially through the collar, and when the collar and screw are in an implant, is prevented from moving out of the implant, even if the screw has dislodged from the bone through which it was inserted. Accordingly, the invention features systems comprising a screw and fixation collar, which may be operably connected together, then further used with an implant such as a spinal implant in order to secure the implant to bone with a substantially diminished risk that the screw will become dislodged from the implant.

Figure 1A:
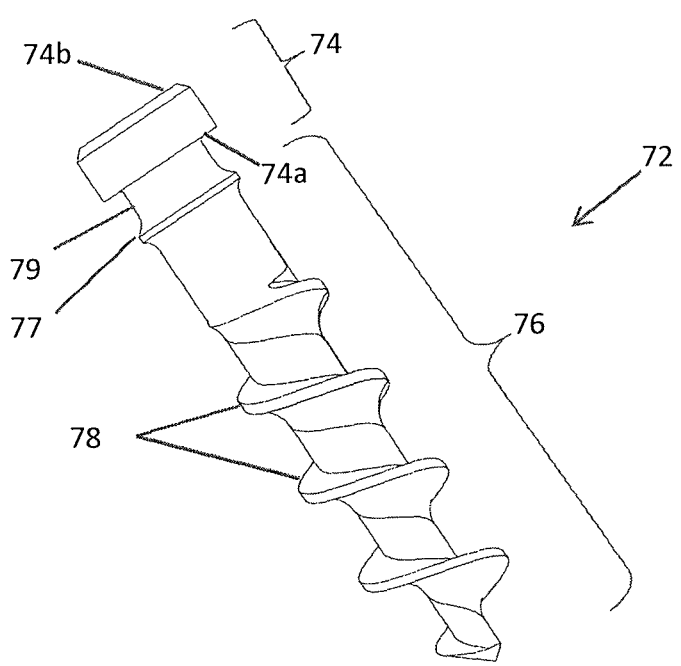
FIG. 1A shows a screw having a collar and groove on the shaft, which are capable of engaging counterpart structures on a fixation collar.

A screw 72 may comprise any type, size, diameter, length, or configuration suitable for use in anchoring implants to bone. An example of a screw 72 is shown in FIG. 1A. The screw 72 may comprise a head 74 and a shaft 76, where at least a portion of the shaft 76 comprises screw threads 78. The head 74 preferably has a wider diameter than the shaft 76. The type and orientation (e.g., left or right orientation) of the threads 78, including the spacing, diameter, and pitch, are not especially restricted and may be readily selected by persons of ordinary skill in the art, depending upon what type and size of spinal implant with which the screw 72 is intended to be used. The screw head 74 has a bottom 74a and a top 74b, and the top 74b may comprise a slot 75, which may comprise any suitable shape, which engages a tool such as a screw driver.

The screw 72 also preferably comprises a shoulder 77, and a groove 79 between the bottom 74a of the screw head 74 and the shoulder 77. The shoulder 77 preferably has an outer diameter that is at least greater than the inner diameter of the groove 79, and the shoulder 77 diameter is also preferably greater than the diameter of the main shaft 76. The diameter of the shoulder 77 is preferably less than the outer diameter of the screw threads 78. The groove 79 has an inner diameter that may be the same as, greater than, or less than the diameter of the main shaft 76. The groove 79 and shoulder 77 may comprise undercuts, which may be curved or radiused, that slope inwardly or outwardly in order to provide for a less sharp transition between the groove 79 and the shoulder 77. The bottom 74a of the screw head 74 and the groove 79 may comprise undercuts, which may be curved or radiused, that slope inwardly or outwardly in order to provide for a less sharp transition between the screw head 74 and the groove 79.

Figure 1B:
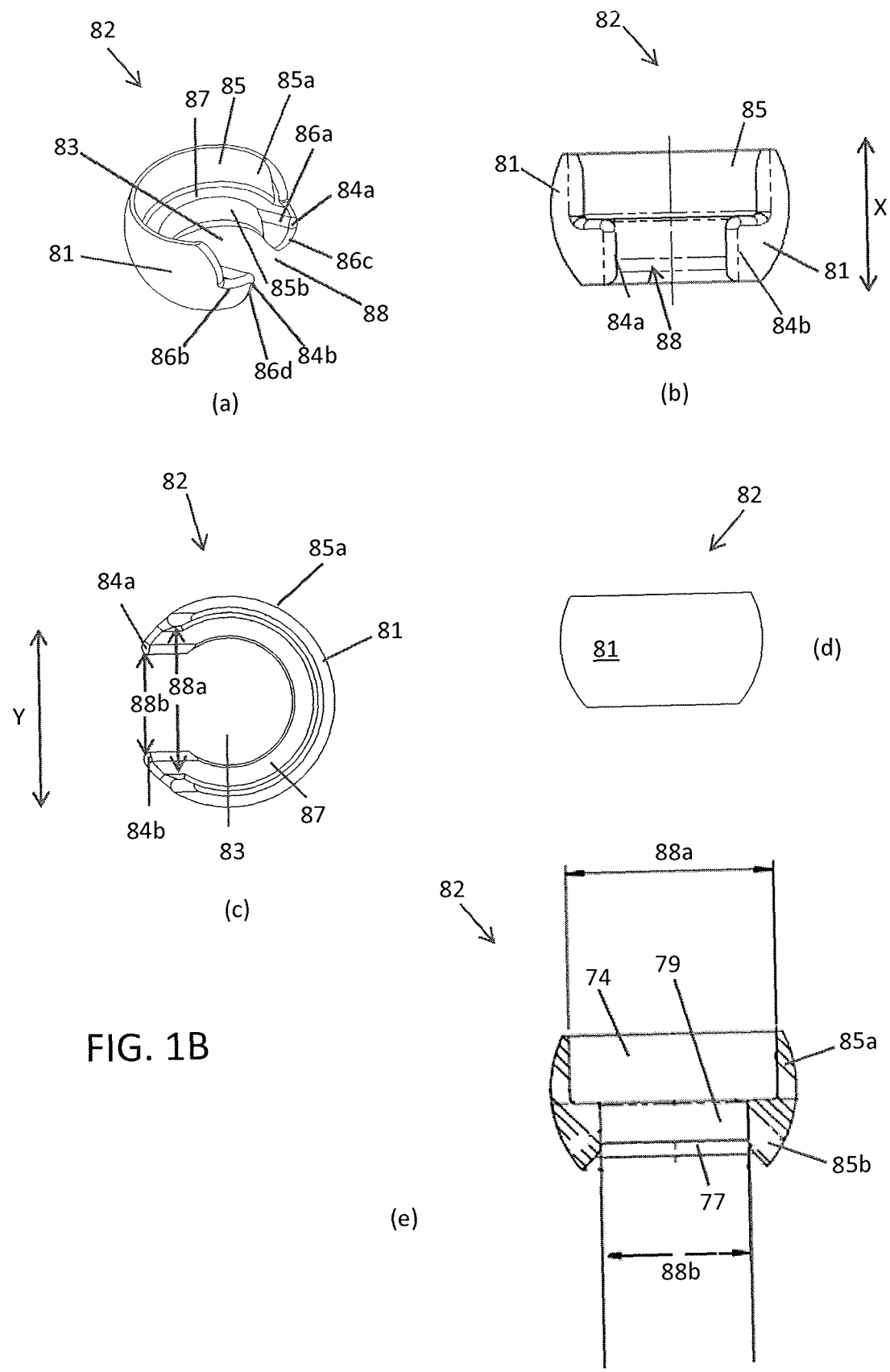
FIG. 1B shows various views of a fixation collar, including (a) a perspective view; (b) a front view; (c) a top view; (d) a back view; and (e) another front view of (b) highlighting additional features of the collar.

A fixation collar 82 is used with the screw 72, particularly in applications in which the screw 72 is used to secure or anchor an implant to bone. The fixation collar 82 is preferably substantially C-shaped, for example, as shown in FIG. 1B(a) and (c). The fixation collar 82 comprises a sidewall 85, that at least partially surrounds a void 83. The void is preferably substantially in the center of the collar 82 and extends along an axis that is parallel to the vertical axis (x axis, FIG. 1B(b)) of the fixation collar. The sidewall 85 may comprise a top portion 85a and a bottom portion 85b. The top portion 85a preferably comprises a recessed portion of the sidewall 85 (recessed internally), with the recessed portion forming a ridge 87 where the area of recession stops. The ridge 87 comprises a region of the collar 82 where the screw head 74 may be seated when the screw 72 is inside of the void 83. The bottom portion 85b of the sidewall 85 is preferably configured to engage the groove 79 of the screw 72 when the screw 72 is inside of the void 83.

Figure 1C:
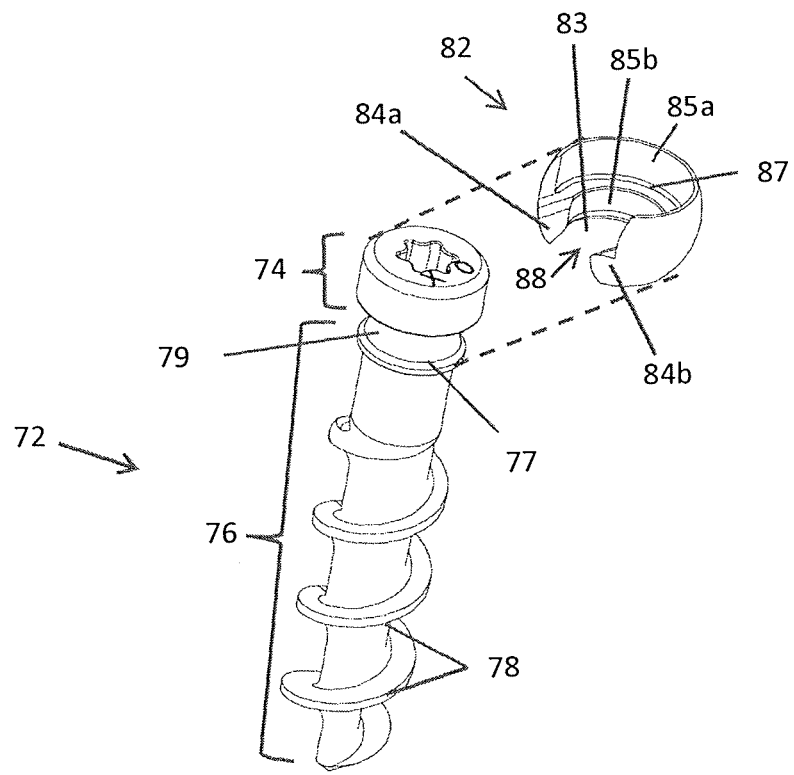
FIG. 1C shows an exploded view of the screw and fixation collar assembly, showing how they are coupled or assembled together.
Figure 1D:
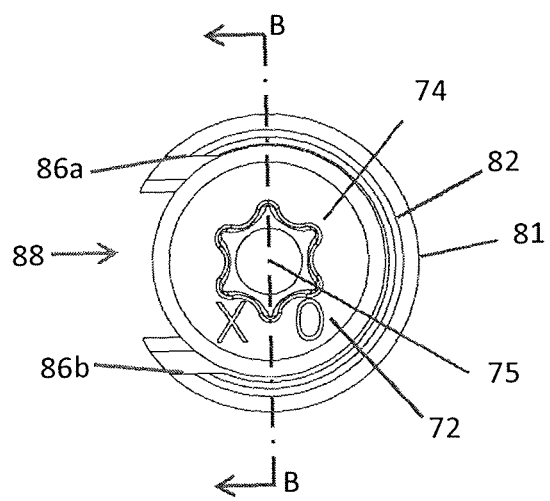
FIG. 1D shows a top view of an assembled screw and fixation collar.
Figure 2A:
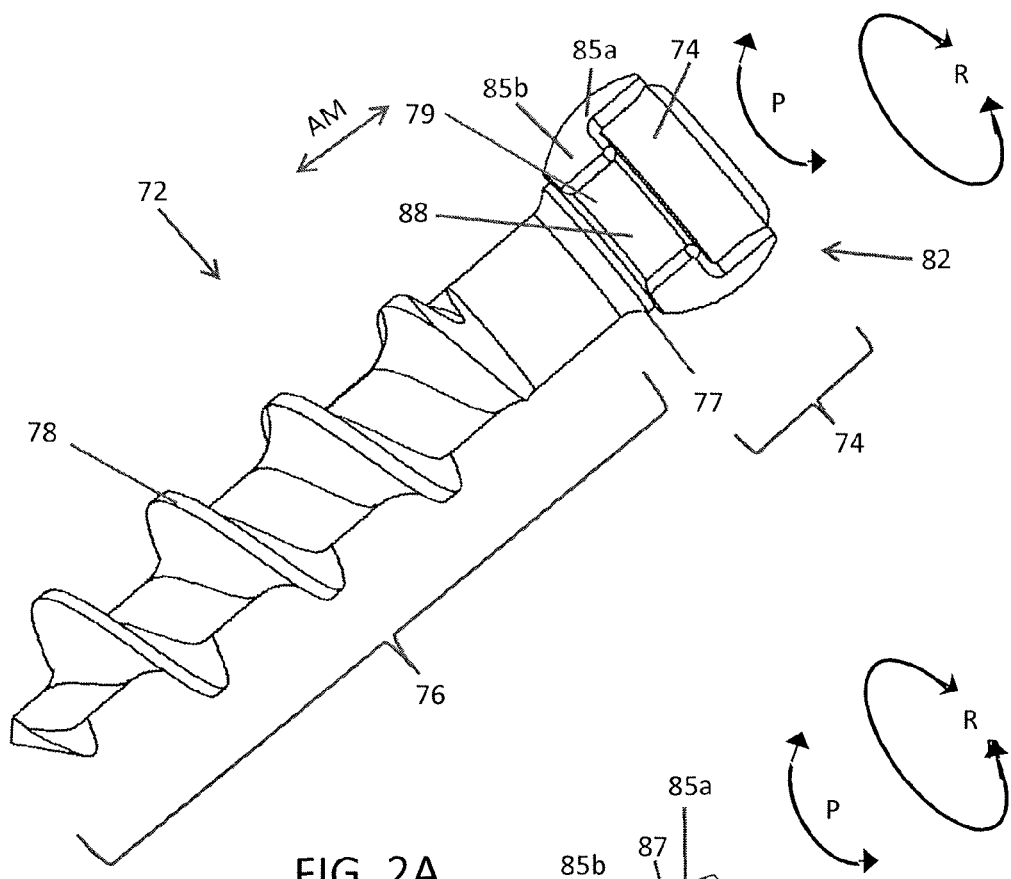
FIG. 2A shows a perspective view of a screw and fixation collar assembly.

Since the fixation collar 82 comprises a C shape, the sidewall 85 comprises two ends 84a, 84b where the sidewall 85 terminates. The ends 84a, 84b, as well as at least some of the regions proximal to the ends 84a, 84b are preferably at least partially flexible along an axis (y axis, FIG. 1B(c)) that is perpendicular to the vertical axis of the fixation collar 82. This flexibility allows the ends 84a, 84b to expand in order to snap fit a screw into the void 83, but the compress back to their original location without remaining permanently expanded. For example, the ends 84a, 84b define a gap 88 between them, which gap 88 is in communication with the void 83. The gap 88 preferably has a width that is slightly narrower than the inner diameter of the groove 79 of the screw 72, such that the screw 72 cannot simply move through the gap 88 and into the void 83 without at least a bit of force. In other words, the ends 84a, 84b obstruct free movement of the screw 72 into and out of the void 83. But the at least partial flexibility of the end regions of the collar 82 (to include at least the ends 84a, 84b and at least a portion of the sidewall 85 beyond the ends 84a, 84b) allows the ends 84a, 84b to expand just enough to allow the screw 72 and, in particular, the groove 79, to pass through the gap 88 and into the void 83 such that the screw 72 and fixation collar 82 may be assembled together (FIG. 1C, FIG. 2A), or out from the void 83 such that the screw 72 and fixation collar 82 may be disassembled. The act of passing the groove 79 through the gap 88 does not permanently displace the position of the ends 84a, 84b, i.e., the ends 84a, 84b return to their original spacing and the gap 88 is not permanently expanded from passing the screw 72 into or out from the void 83. Once the screw 72 is passed through the gap 88, the ends 84a, 84b thus partially enclose the groove 79, thereby retaining the groove 79 in the void 83, albeit preferably reversibly.

The gap 88 may be about 1 mm to about 3 mm in width. In some aspects, the gap 88 may be about 2 mm to about 3 mm in width. In some aspects, the gap 88 may be about 2 mm to about 2.5 mm in width. In some aspects, the gap 88 may be about 2 mm to about 2.2 mm in width. In some aspects, the gap 88 may be about 2.1 mm in width.

It is highly desirable that the screw 72, once engaged with the fixation collar 82, not be able to move axially through the void 83. It is also desirable that the screw 72 not be able to move axially through the void 83 in order to engage the screw 72 with the fixation collar 82. Thus, the void 83 preferably has a diameter narrower than the outer diameter of the shoulder 77. Although it may be possible to angle the fixation collar 82 in a way that the screw 72 may be partially rotated through the void 83, the shoulder 77 is prevented from passing beyond the ridge 87 such that the screw 72 is unable to completely move through the void 83. In addition, once the screw 72 and collar 82 are properly engaged, with the lower sidewall portion 85b engaging the groove 79, the lower portion 85b prevents the shoulder 77 from passing beyond the bottom or the lower sidewall portion 85b such that the screw 72 may not be backed out or otherwise rotated out of the collar 82. The lower portion 85b may comprise undercuts that are compatibly shaped with the undercuts of the groove 79 (FIG. 1B(e)).

Figure 3A:
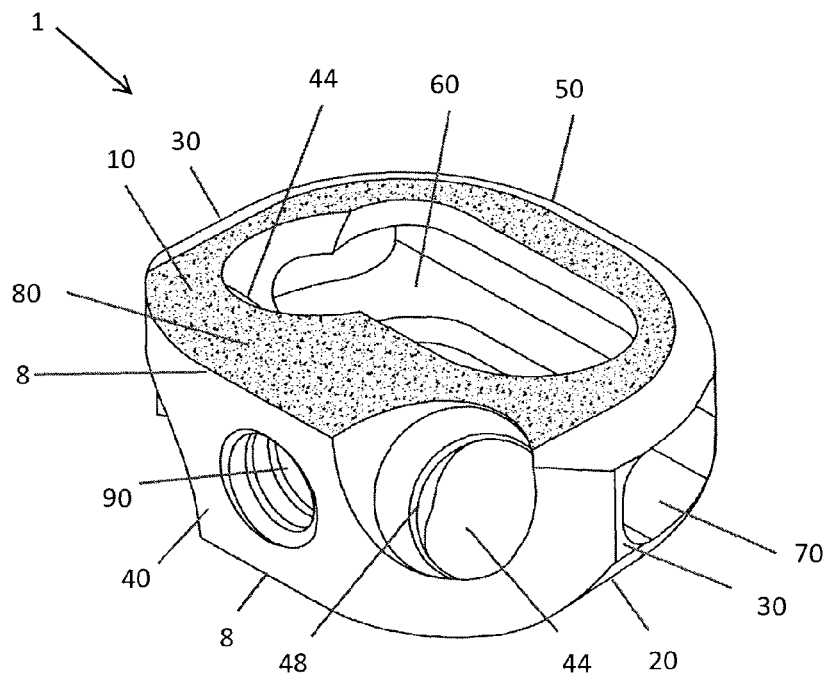
FIG. 3A shows a perspective view of an interbody spinal implant including apertures for a screw and fixation collar.
Figure 3B:
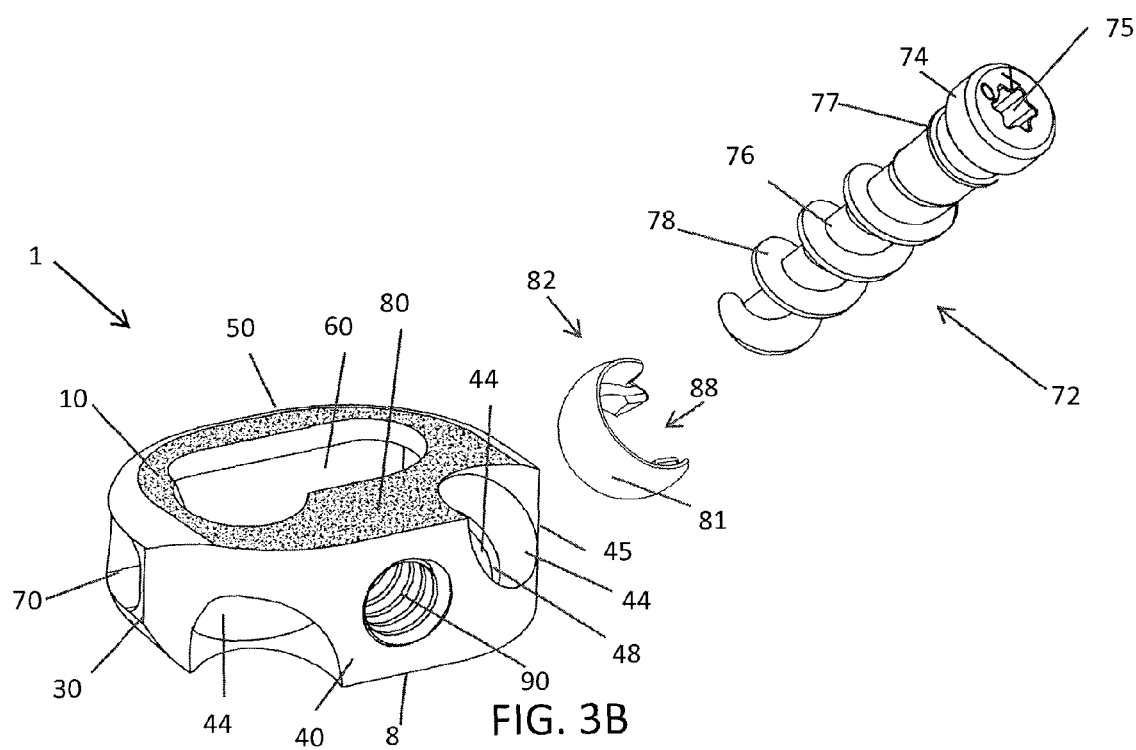
FIG. 3B shows an exploded view of an interbody spinal implant, screw, and fixation collar.
Figure 5A:
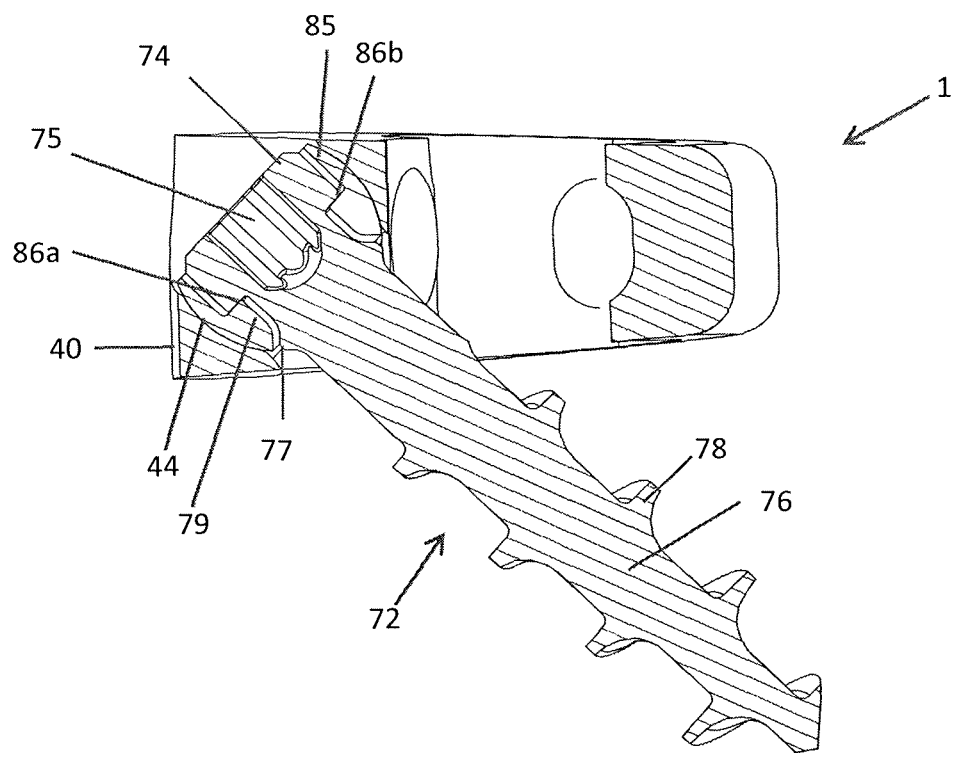
FIG. 5A shows a cross-sectional view of an implant, screw and fixation collar for example, taken along line A-A (FIG. 4B) and looking in the direction of the arrows.
Figure 5B:
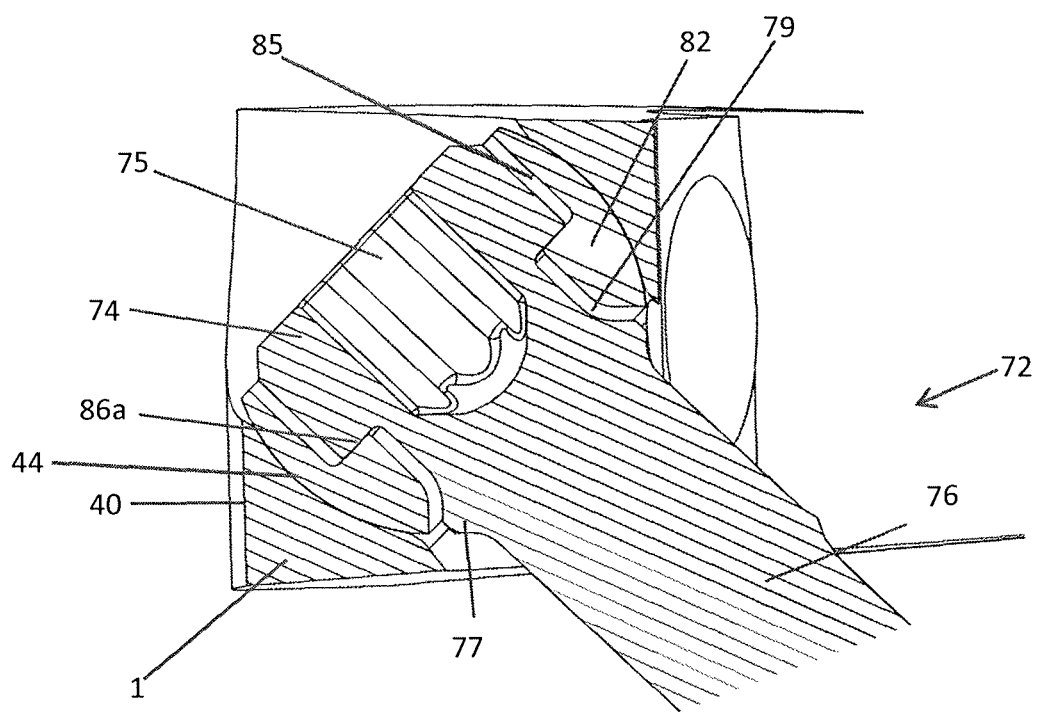
FIG. 5B provides a close-up view of FIG. 5A.

The sidewall 85 preferably comprises a convex-shaped outer surface 81 (FIG. 1B(a) and (d)). The convex shape is configured in a way for the fixation collar 82 to engage a compatible aperture 44, 144, and 244 present in an implant (see, e.g., FIGS. 3A and 3B). The aperture 44, 144, and 244 preferably comprises concave sidewalls in the body of the implant, and the size, shape, pitch, and camber of the concave sidewalls are preferably essentially the negative of the size, shape, pitch, and rocker of the convex outer surface 81. The compatibility of the aperture 44, 144, and 244 and collar 82 allow limited pivotal and rotational movement of the screw 72 and fixation collar 82 (as assembled together) about the aperture 44. However, the size and shape of the aperture 44, 144, and 244 inhibits axial movement of the screw 72 and fixation collar 82 such that the screw 72 and fixation collar 82 are substantially prevented from moving further into the implant body and are substantially prevented from moving out of the aperture 44, 144, and 244 once engaged. See, FIGS. 5A and 5B. Load bearing forces and movement of the body should not be capable of disengaging the screw 72 and fixation collar 82 from the aperture 44, 144, and 244. Nevertheless, in some aspects, it is desired that the screw 72 and fixation collar 82 be removable from the aperture 44, 144, and 244 such that the engagement is not permanent. Preferably, any disengagement from the aperture 44, 144, and 244 would necessitate intervention with tools appropriate for the disengagement.

Each end 84a, 84b of the sidewall 85 preferably comprises a notch 86a, 86b in the upper portion 85a. Each notch 86a, 86b is thus above the ridge 87. Each notch 86a, 86b may define a ledge in the ridge 87, which ledge is essentially a portion of the ridge 87 exposed because a portion of the sidewall 85 is missing per the notch 86a, 86b. The ridge preferably comprises blunt and radiused edges, and preferably does not come to a sharp point at the end 84a, 84b. In highly preferred aspects, each notch 86a, 86b is radiused in a direction away from the gap 88 (FIG. 1B(a)). Thus, for example, each notch 86a, 86b in the top portion 85a of the sidewall 85 may comprise a curved "cut-out" of the sidewall 85. The curvature in the notch 86a, 86b substantially reduces unwanted snagging of the edges of the notch 86a, 86b on the edges of flutings 64 of the concave implant apertures 44, 144, and 244 (see, FIGS. 14B and 14C). Such snagging may cause the collar 82 to dig into the body of the implant, and potentially erode away portions of the implant body thereby dislodging implant material into the patient. Each notch 86a, 86b also offers an additional advantage of allowing the collar 82 to more easily come off of the screw 72.

Each end 84a, 84b of the sidewall 85 preferably comprises a notch 86c, 86d in the lower portion 85b. Each notch 86c, 86d is thus below the ridge 87. In highly preferred aspects, each notch 86c, 86d is radiused in a direction away from the gap 88 (FIG. 1B(a)). Thus, for example, each notch 86c, 86d in the bottom portion 85b of the sidewall 85 may comprise a curved "cut-out" of the sidewall 85. Each notch 86c, 86d also offers an additional advantage of allowing the collar 82 to more easily come off of the screw 72.

Since the notches 86a, 86b on the upper portion 85a of the sidewall 85 are preferably set back from the ends 84a, 84b, these notches 86a, 86b effectively enlarge the gap 88, at least as concerns the gap 88 between the ends 84a, 84b at the upper portion 85a, above the ridge. See, e.g., FIG. 1B(c), shown as smaller gap 88b (lower portion) and larger gap 88a (upper portion). The particular difference in gap width can vary. Thus, in some aspects, the width of the gap 88 above the ridge 87 is about 10% to about 60% greater than the width of the gap 88 below the ridge 87. In some aspects, the width of the gap 88 above the ridge 87 is about 15% to about 55% greater than the width of the gap 88 below the ridge 87. In some aspects, the width of the gap 88 above the ridge 87 is about 30% to about 50% greater than the width of the gap 88 below the ridge 87. In some aspects, the width of the gap 88 above the ridge 87 is about 25% to about 45% greater than the width of the gap 88 below the ridge 87. In some aspects, the width of the gap 88 above the ridge 87 is about 30% to about 40% greater than the width of the gap 88 below the ridge 87. In some aspects, the width of the gap 88 above the ridge 87 is about 38% to about 32% greater than the width of the gap 88 below the ridge 87. In some aspects, the width of the gap 88 above the ridge 87 is about 37% to about 35% greater than the width of the gap 88 below the ridge 87.

Figure 2B:
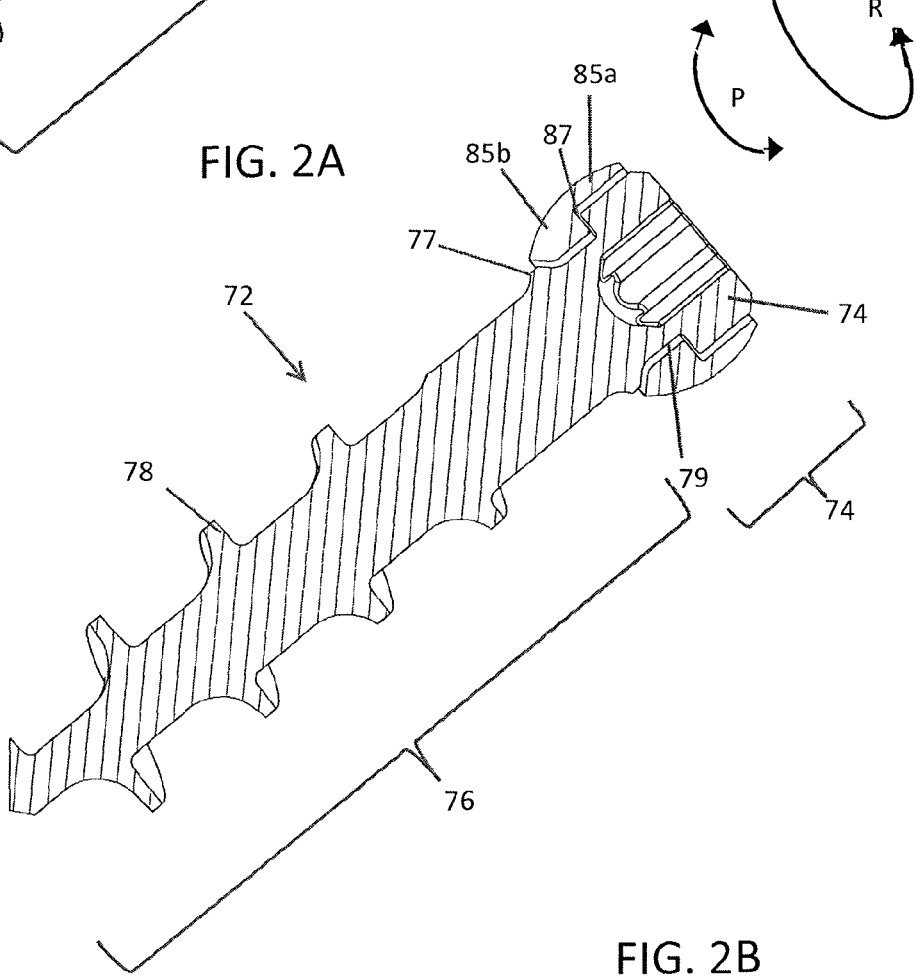
FIG. 2B shows a cut-away view of a screw and a fixation collar assembly.

When the fixation collar 82 is coupled with the screw 72, the lower portion 85b of the sidewall 85 is received in the groove 79 of the screw 72 and the screw head 74 is received in the upper portion 85a of the sidewall 85. The ridge 87 and shoulder 77 substantially inhibit axial movement (FIG. 2A, arrow AM) of the screw 72 relative to vertical axis of the collar 82. Nevertheless, the head 74 and groove 79 of the screw respectively comprise a diameter that fits within the appropriate spaces in the sidewall 85 such that the screw 72 may freely rotate and partially pivot (FIGS. 2A and 2B, arrows R and P) within the void 83 surrounded by sidewall 85, but the screw 72 may not exit the gap 88 on its own accord.

The screw 72 and/or the fixation collar 82 may comprise any biocompatible material. The material may comprise a plastic, silicone, or a polymer (e.g., polyether ether ketone (PEEK) or ultra-high molecular weight polyethylene (UHMWPE)), or a composite. Other examples of suitable materials include urethane dimethacrylate (DUDMA)/tri-ethylene glycol dimethacrylate (TEDGMA) blended resin, and a plurality of fillers and fibers including bioactive fillers and E-glass fibers. In some aspects, the material may comprise a metal. The metal may comprise titanium, an alloy of titanium such as an aluminum and vanadium alloy of titanium (e.g., 6-4), a nickel alloy of titanium such as nitinol, a cobalt chromium alloy, or surgical grade steel. The screw 72 and/or fixation collar 82 may be comprised of allogenic or cortical bone. The screw 72 and/or fixation collar 82 may be comprised of a ceramic.

The screw 72 and fixation collar 82 are suitable for use in anchoring implants to bone, including enhancing the securement of an implant in place. The screw 72 is inserted into bone adjacent to the implant, thereby fixing the implant in place. The fixation collar 82 substantially inhibits the screw 72 from backing out of the implant and, thus, also substantially inhibits the screw 72 from backing out of the bone in which the screw 72 is embedded. The screw 72 and fixation collar 82 are suitable for use with any implant. In some highly preferred aspects, the screw 72 and fixation collar 82 are used with intervertebral implants, which are implanted between adjacent vertebrae. In some highly preferred aspects, the screw 72 and fixation collar 82 are used with spinal motion segment implants, which are implanted in place of removed sections of adjacent vertebrae, including the interspersed discs.

FIGS. 3A, 6B, 8A, and 13A show non-limiting examples of intervertebral implants 1, 1a, 101, 201, respectively, suitable for use with a screw 72 and fixation collar 82 assembly as described and exemplified herein. Since the basic required features of suitable implants are the same among the embodiments, they and their features will be described hereinafter collectively in an attempt to keep this description concise where appropriate.

More particularly, certain embodiments of the interbody implants 1, 1a, 101, and 201 have a generally oval-shaped transverse cross-sectional area (e.g., FIG. 3A), which may be suitable for Anterior Lumbar Interbody Fusion (ALIF). The implant 101 may have a generally rectangular transverse cross-sectional area (e.g., FIG. 13A) suitable for Posterior Lumbar Interbody Fusion (PLIF). The implant 201 may have a generally t-shape (e.g., FIG. 8A) suitable for lateral fusion. The implant may be generally circular in shape suitable for cervical fusion. The implants 1, 1a, 101, and 201 may be shaped to reduce the risk of subsidence, and improve stability, by maximizing contact with the apophyseal rim of vertebral endplates.

The spinal implant 1, 1a, 101, and 201 comprise basic structural features that include, without limitation, a top surface 10, 110, and 210, a bottom surface 20, 120, and 220, a posterior portion 50, 150, and 250, an anterior portion 40, 140, and 240, opposing lateral sides 30, 130, and 230, a single vertical aperture 60, 160, and 260 extending from the top surface 10, 110, and 210 to the bottom surface 20, 120, and 220, having a size and shape for maximizing the surface area of the top surface 10, 110, and 210 and the bottom surface 20, 120, and 220 available proximate the anterior portion 40, 140, and 240 and posterior portion 50, 150, and 250, optionally one or more transverse apertures 70, 170, and 270 through at least one of the lateral sides 30, 130, and 230, extending into a substantially hollow center, and optionally an opening 90, 190, and 290, for example, in the anterior portion 40, 140, and 240 or posterior portion 50, 150, and 250, which may be configured to engage a tool to assist in placement and/or positioning of the implant in the intervertebral space. The transverse aperture 70, 170, and 270 may be broken into two, separate sections by an intermediate wall. These structural features are shown throughout the drawings, for example, FIG. 4A, 4B, 6B, 8A, 13A.

Certain embodiments of the interbody implant 1, 1a, 101, and 201 are substantially hollow. The substantially hollow portion may be filled, for example, with cancellous autograft bone, allograft bone, demineralized bone matrix (DBM), porous synthetic bone graft substitute, bone morphogenic protein (BMP), or combinations of those materials.

The top surface 10, 110, and 210 and bottom surface 20, 120, and 220 may comprise a transverse rim having varying width or thickness, and a maximum width at its center, which rim is defined by the single vertical aperture 60, 160, and 260, as positioned between the anterior portion 40, 140, and 240, posterior portion 50, 150, and 250, and opposing lateral sides 30, 130, and 230. The transverse rim comprises a blunt and radiused portion along the top and/or bottom of the anterior portion 40, 140, and 240 or posterior portion 50, 150, and 25, and along the top of the lateral sides 30, 130, and 230. In addition to the blunt and radiused portion, the transverse rim of the top surface 10, 110, and 210 and the bottom surface 20, 120, and 220 includes a portion that is not blunt and radiused. This non-blunt and non-radiused portion has a roughened surface topography 80, 180, and 280. The roughened surface topography 80, 180, and 280 preferably is not sharp teeth or that dig into, score, and otherwise damage bone structures. Rather, the roughened surface topography 80, 180, and 280 is adapted to grip bone, inhibit migration of the implant 1, 1a, 101, and 201, and preferably promote biological and chemical fusion (e.g., a biostimulating effect). The roughened surface topography 80, 180, and 280 preferably comprises a bioactive surface, which stimulates and/or enhances bone growth and osteointegration of the implant 1, 1a, 101, and 201 with the surrounding bone structures. The roughened surface topography 80, 180, and 280 comprises macro-, micro-, and nano-scale structures, preferably in regular and repeating patterns.

Figure 8A:
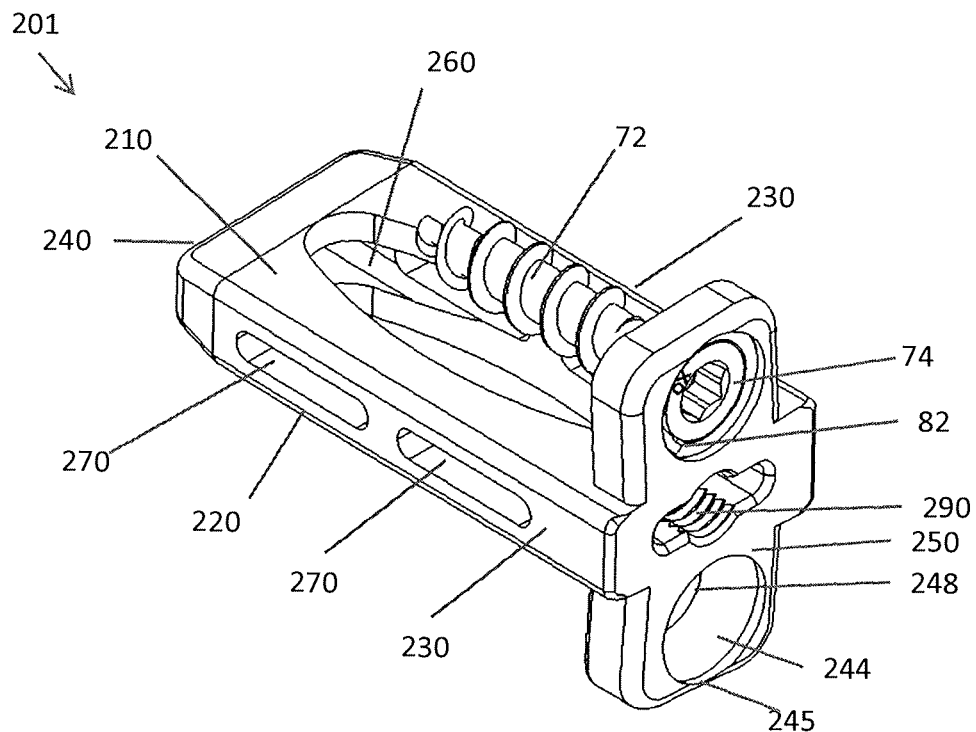
FIG. 8A shows a perspective view of a lateral implant, screw, and fixation collar assembly.
Figure 8B:
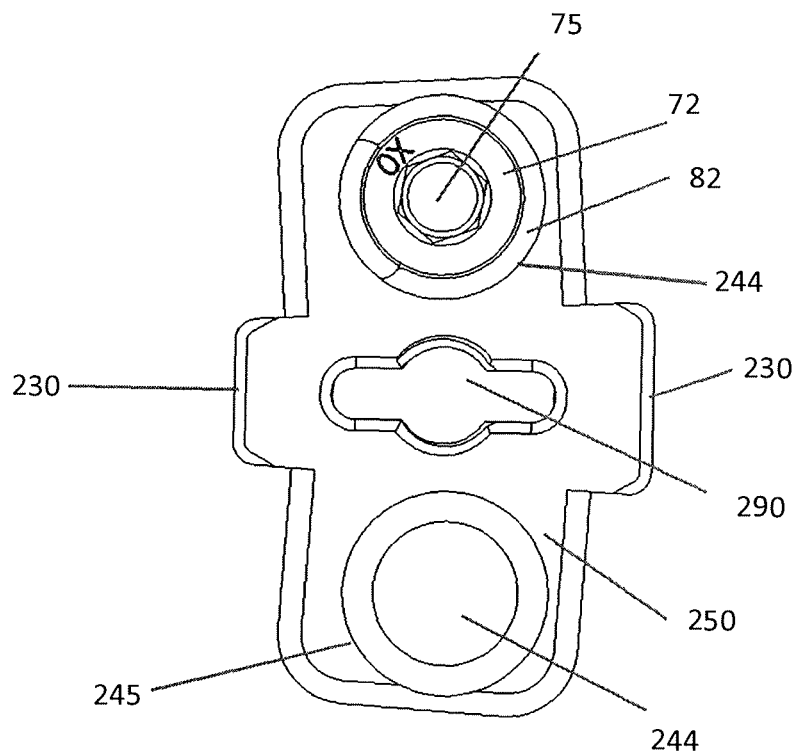
FIG. 8B shows a front view of a lateral implant, screw, and fixation collar assembly.

In the case of the t-shaped implant 201, for example, as depicted in FIG. 8A, the implant 201 may be approximately t-shaped such that the posterior portion 250 is expanded to include a first extension 252 extending beyond the top surface 210 and a second extension 254 extending beyond the bottom surface 220. The top and bottom surfaces 210, 220 may be configured to sit between two adjacent vertebrae whereas the first and second extensions 252, 254 may extend along the outside of the vertebrae.

The implant 1, 1a, 101, and 201 may also have a lordotic angle to facilitate alignment with the spinal column. Depending on the type of implant 1, 1a, 101, and 201, one lateral side 30, 130, and 230 is preferably generally greater in height than the opposing lateral side 30, 130, and 230 or the anterior portion 40, 140, and 240 may be generally greater in height than the opposing posterior portion 50, 150, and 250, or vice versa. The lordotic angle may allow the implant 1, 1a, 101, and 201 to better compensate for the generally less supportive bone found in certain regions of the vertebral endplate. As much as seven to fifteen degrees of lordosis (or more) may be built into the implant 1, 1a, 101, and 201.

To enhance movement resistance and provide additional stability under spinal loads in the body, the implant 1, 1a, 101, and 201 may comprise one or more anti-expulsion edges 8, 108, and 208 that tend to "dig" into the end-plates slightly and help to resist expulsion. The one or more anti-expulsion edges 8, 108, and 208 may be present on the top surface 10, 110 and 210; the bottom surface 20, 120 and 210; or both surfaces of the implant 1, 101 and 210. The one or more anti-expulsion edges 8, 108, and 208 may be present at the edge of the anterior portion 40, 140, and 240 or edge of the posterior portion 50, 150, and 250. The one or more anti-expulsion edges 8, 108, and 208 may also be present on the anterior or posterior edges of the single vertical aperture 60, 160, and 260.

For use with the screw 72 and fixation collar 82 assembly, an implant, including an intervertebral implant 1, 1a, 101, and 201 preferably comprises one or more apertures 44, 144, and 244. The one or more apertures 44, 144, and 244 may be through one or more of the top surface 10, 110, and 201, bottom surface 20, 120, and 220, anterior portion 40, 140, and 240, posterior portion 50, 150, and 250, or opposing lateral sides 30, 130, and 230. See, e.g., FIGS. 4A, 4B, 6A, 6B, 8A, 8B, 9A, 10A, 10B, 13A, and 14A-C. The one or more apertures 44, 144, and 244 essentially bore through the sidewalls of the implant 1, 1a, 101, and 201 at an angle that would allow the screw 72 to pass through the implant 1, 1a, 101, and 201 body and into adjacent bone, not unlike "toenailing" used in carpentry. Each aperture 44, 144, and 244 preferably comprises concave sidewalls that closely approximate the convex outer surface 81 of the fixation collar 82 sidewall 85. In this manner, the screw 72 and fixation collar 82 are assembled together, then the screw 72 is inserted into the aperture 44, 144, and 244 and driven into the bone. As the screw is driven into the bone, eventually the fixation collar 82 (which is connected to the screw head 74 and groove 79) passes into the aperture 44, 144, and 244, in a type of snap-fit. Once the fixation collar 82 is fully inside of the aperture 44, 144, and 244, the aperture 44, 144, and 244 will inhibit axial movement of the screw 72 and fixation collar 82, particularly out from the aperture 44, 144, and 244 which, in turn, inhibits axial movement of the screw 72 out of the bone. The one or more apertures 44, 144, and 244 are preferably positioned on the implant 1, 1a, 101, and 201 to provide for proper visualization and access by a practitioner performing an implantation procedure, and for maximum fixation between the implant 1, 1a, 101, 201 and the adjacent bone.

Figure 4A:
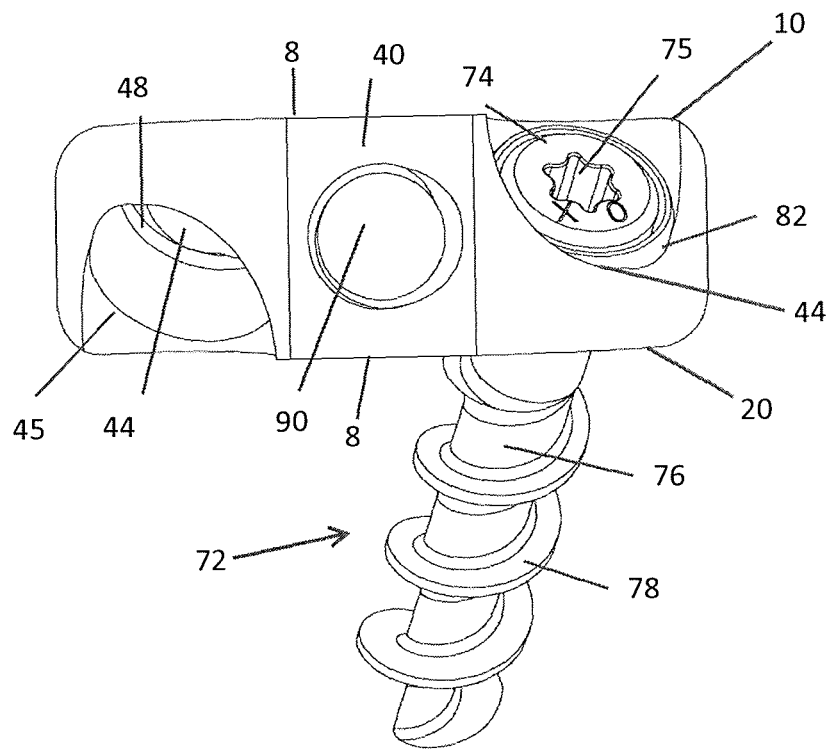
FIG. 4A shows a side view of an assembled implant, screw and fixation collar.
Figure 4B:
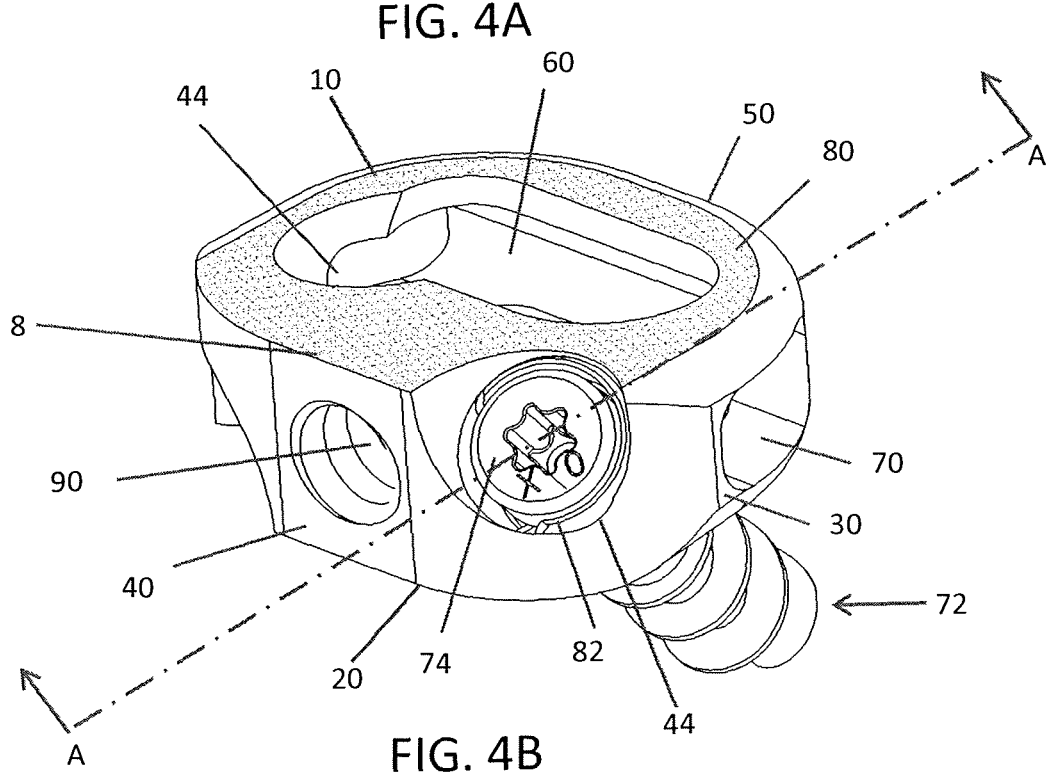
FIG. 4B shows a perspective view of an assembled implant, screw and fixation collar.
Figure 6A:
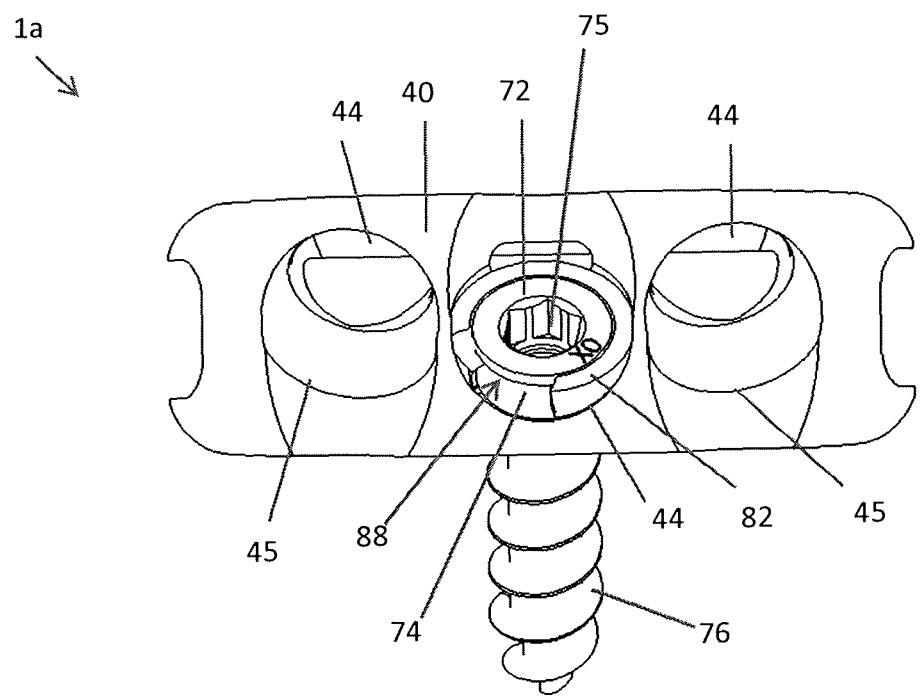
FIG. 6A shows a front view of an ALIF implant, screw, and fixation collar.
Figure 6B:
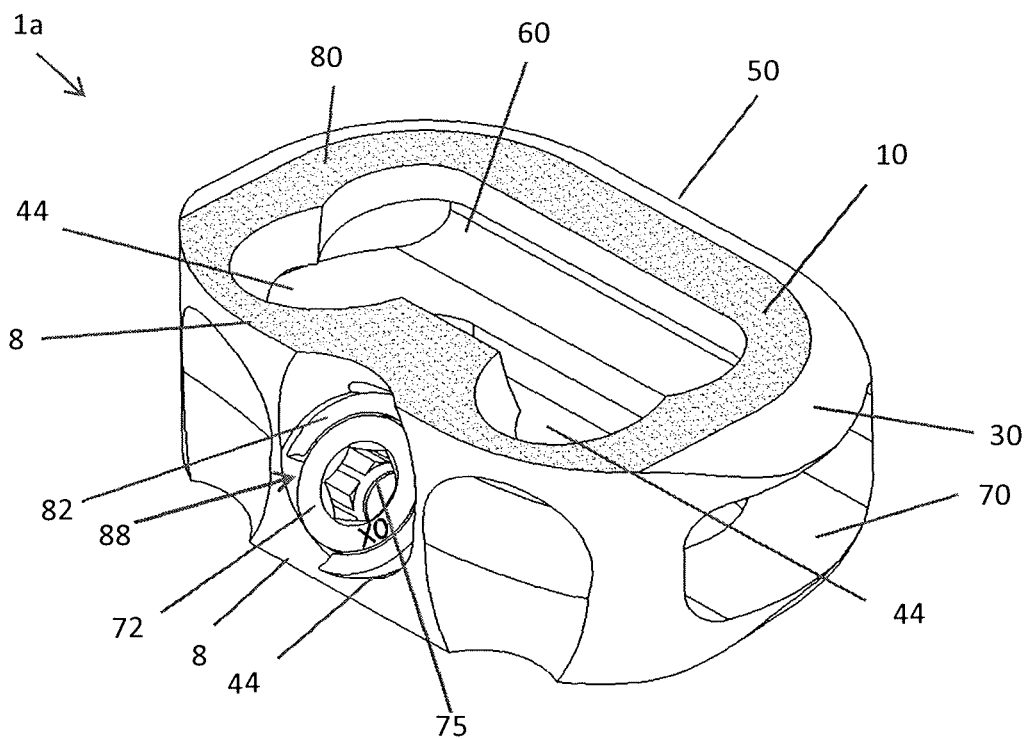
FIG. 6B shows a perspective view of an ALIF implant, screw, and fixation collar.
Figure 7:
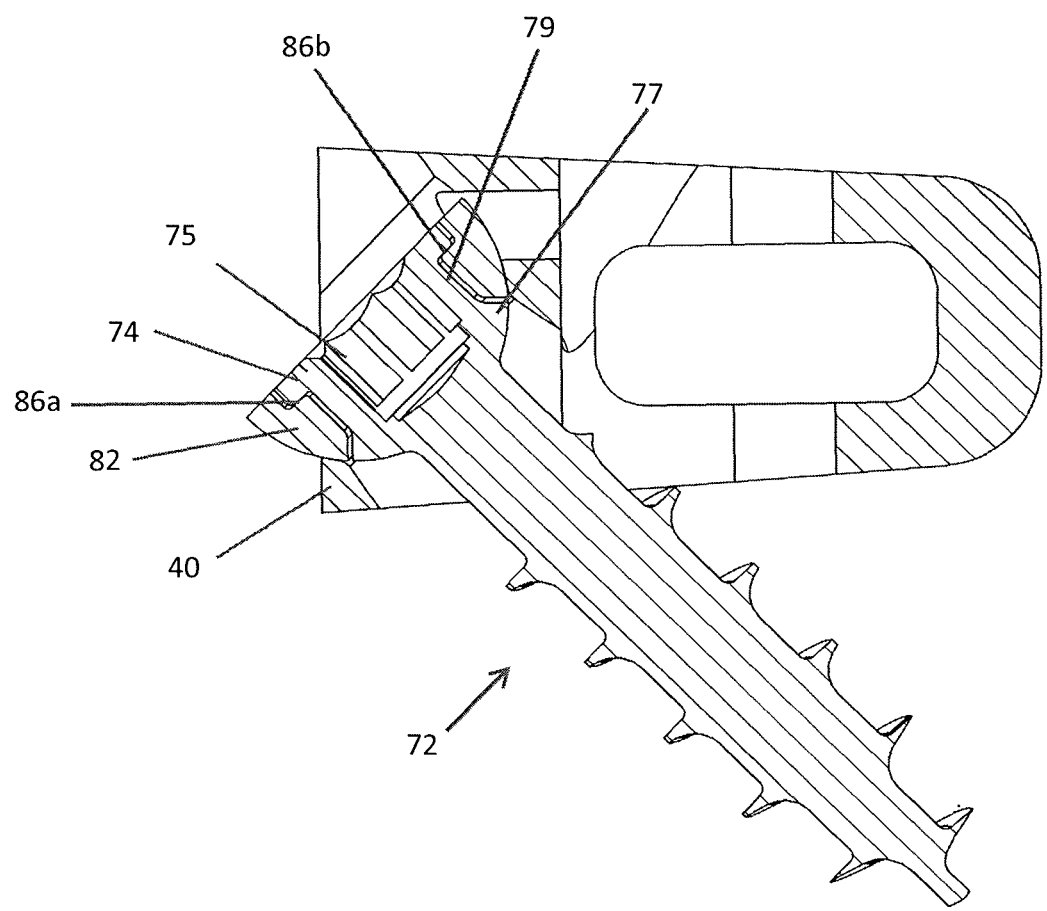
FIG. 7 shows a cross-section view of the an ALIF implant, screw, and fixation collar assembly depicted in FIG. 6B.
Figure 9A:
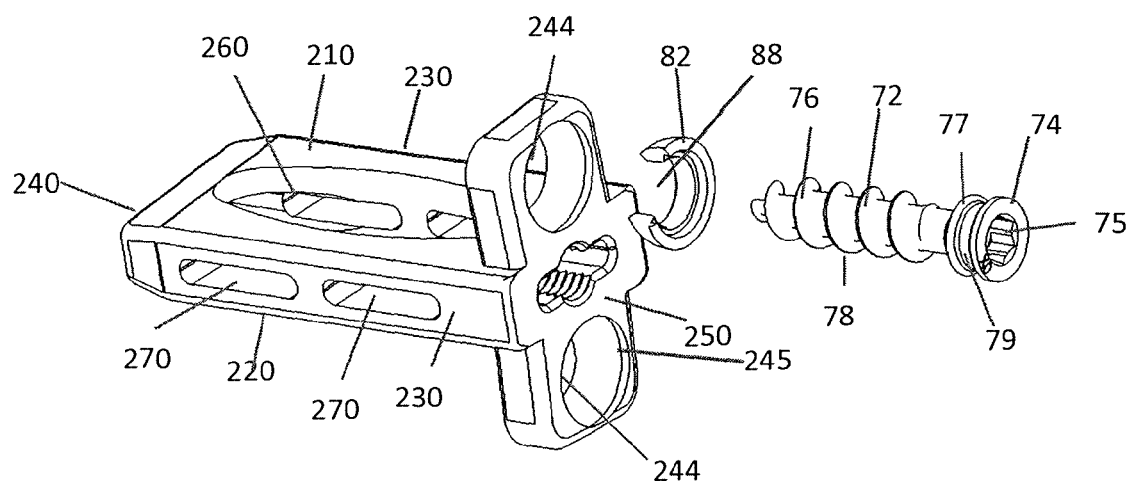
FIG. 9A shows an exploded view of the lateral implant, screw, and fixation collar assembly depicted in FIG. 8A.
Figure 9B:
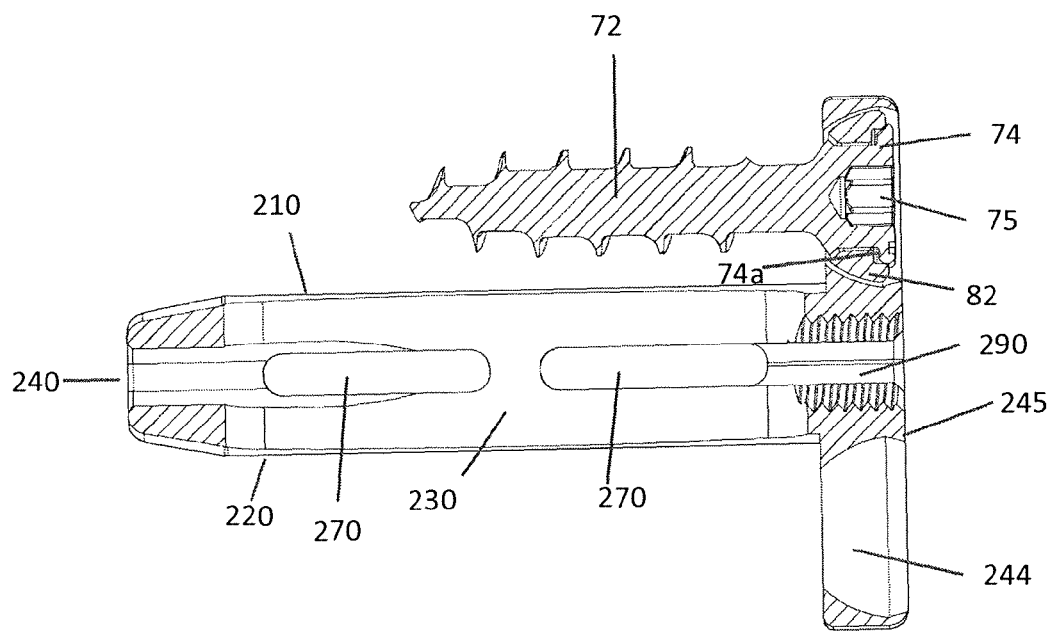
FIG. 9B shows a cross-sectional view of the a lateral implant, screw, and fixation collar assembly depicted in 8A.
Figure 10A:
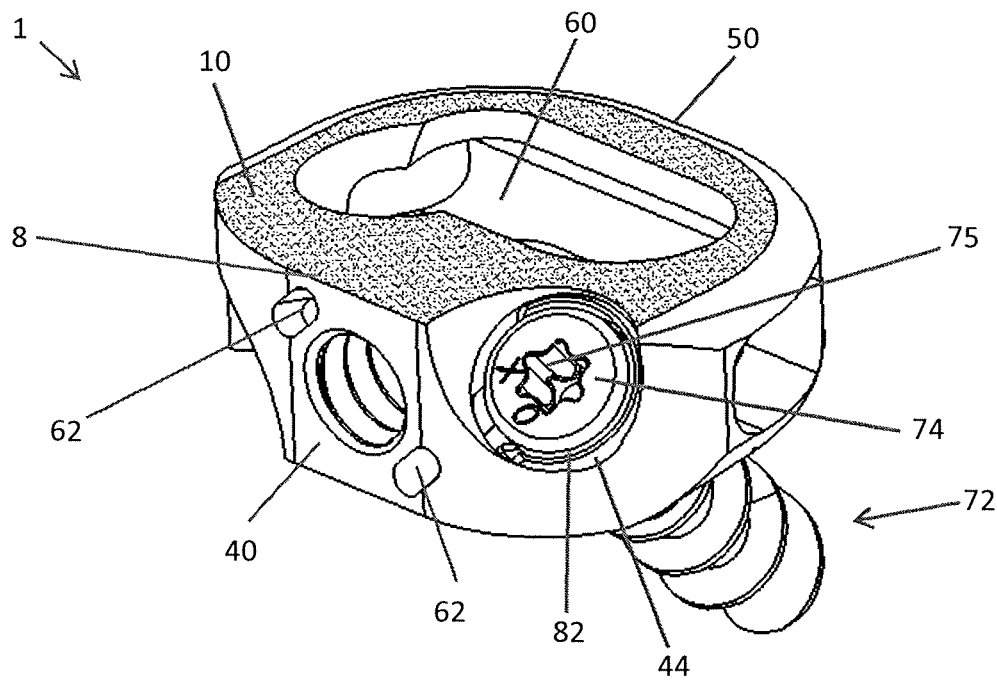
FIG. 10A shows an implant including screw removal slots.
Figure 10B:
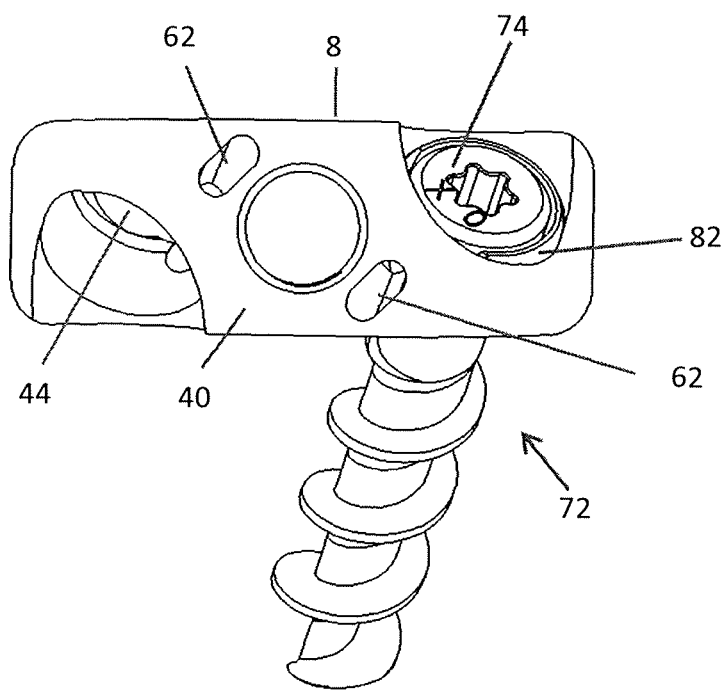
FIG. 10B shows a front view of an implant including screw removal slots.

In some aspects, the one or more apertures 44, 144, and 244 and the corresponding insertion path of the screws 72 are positioned at an angle of about 30° to about 60° of the vertical axis of the implant 1, 1a, 101, and 201. Angles less than about 30° or greater than about 60° may be used in some aspects. The degree of angling may be a function of the implant size or type, or of particular patient characteristics, or of the location or position of the implant once implanted. In some aspects, the implant 1, 1a, 101, and 201 comprises one aperture 44, 144, and 244, configured for the screw 72 to extend through the top 10, 110, and 210 and embed in the upper vertebrae (FIG. 13B), or through the bottom 20, 120, and 220 and embed in the lower vertebrate (FIG. 13A). In some aspects, the implant 1, 1a, 101, and 201 comprises at least two apertures 44, 144, and 244, with one aperture 44, 144, 244 configured for the screw 72 to extend through the top 10, 110, and 210 and embed in the upper vertebrae, and the other aperture 44, 144, and 244 configured for the screw 72 to extend through the bottom 20, 120, and 220 and embed in the lower vertebrate (FIGS. 10A and 10B; and FIG. 7). The one or more apertures 44, 144, and 244 may be in communication with the single vertical aperture 60, 160, and 260, for example, as shown in FIGS. 4B and 6B. In some aspects, the implant 1, 1a, 101, and 201 comprises at least three apertures 44, 144, and 244, with two apertures 44, 144, 244 configured for the screws 72 to extend through the top 10, 110, and 210 and embed in the upper vertebrae, and the third aperture 44, 144, and 244 configured for the screw 72 to extend through the bottom 20, 120, and 220 and embed in the lower vertebrate (FIGS. 6A and 6B). In some aspects, the implant 1, 1a, 101, and 201 comprises at least two apertures 44, 144, and 244, with both aperture 44, 144, 244 configured for the screws 72 to extend through the posterior portion 50, 150, and 250, and one screw 72 embeds in the upper vertebrae, and the other screw 72 embeds in the lower vertebrate (FIGS. 9A and 9B).

The complimentary configuration of the convex outer surface 81 of the fixation collar 82 and the concave inner surfaces of the one or more apertures 44, 144, and 244 of the implant, 1, 101, 201 that allow, after assembly of the screw 72, the fixation collar 82 and the implant 1, 1a, 101, 201, rotational and pivotal movement of the screw 72 and collar 82 within the aperture 44, 144, 244. In some aspects, the aperture 44, 144, and 244 may include a retaining ridge 48, 148, and 248 (see, e.g., FIGS. 1A, 1B, 6A), that may help to retain the fixation collar 82 in the aperture 44, 144, and 244.

The aperture 44, 144, and 244 comprises an opening 45, 145, and 245 on the external surface of the implant 1, 1a, 101, and 201 through which the screw 72 and fixation collar 82 are inserted into the aperture 44, 144, and 244. The opening 45, 145, and 245 of the aperture 44, 144, and 244 is preferably slightly narrower in diameter than the diameter of the widest point of outer surface 81 of the collar 82. This narrowed diameter prevents the fixation collar 82, once seated in the aperture 44, 144, and 244 from expelling out of the implant 1, 1a, 101, and 201. The flexibility of the fixation collar 82 allows the fixation collar 82 to compress sufficiently to pass through the narrowed opening 45, 145, and 245, then expand back to its non-compressed configuration within the aperture 44, 144, and 244; once re-expanded, the fixation collar 82 remains seated in the aperture 44, 144, and 244, unable to pass back out through the opening 45, 145, and 245.

In preferred aspects, when the screw 72 and fixation collar 82 are fully inserted into the aperture 44, 144, and 244, no portion of the screw 72 or fixation collar 82 protrudes outside the footprint of the implant 1, 1a, 101, and 201. For example, no portion of the screw 72 or fixation collar 82 protrudes outside of the plane of the anterior 40, 40a, 140, and 240, posterior 50, 50a, 150, and 250, or lateral sides 30, 30a, 130, and 230 of the implant 1, 1a, 101, and 201. Thus, the screw head 74 and top portion 85a of the collar 82 sidewall 85 may be substantially flush with the implant surfaces so as to minimize tissue impingement and interference with other devices that may be implanted with the implant 1, 1a, 101, and 201 such as plates (not shown).

Figure 22:
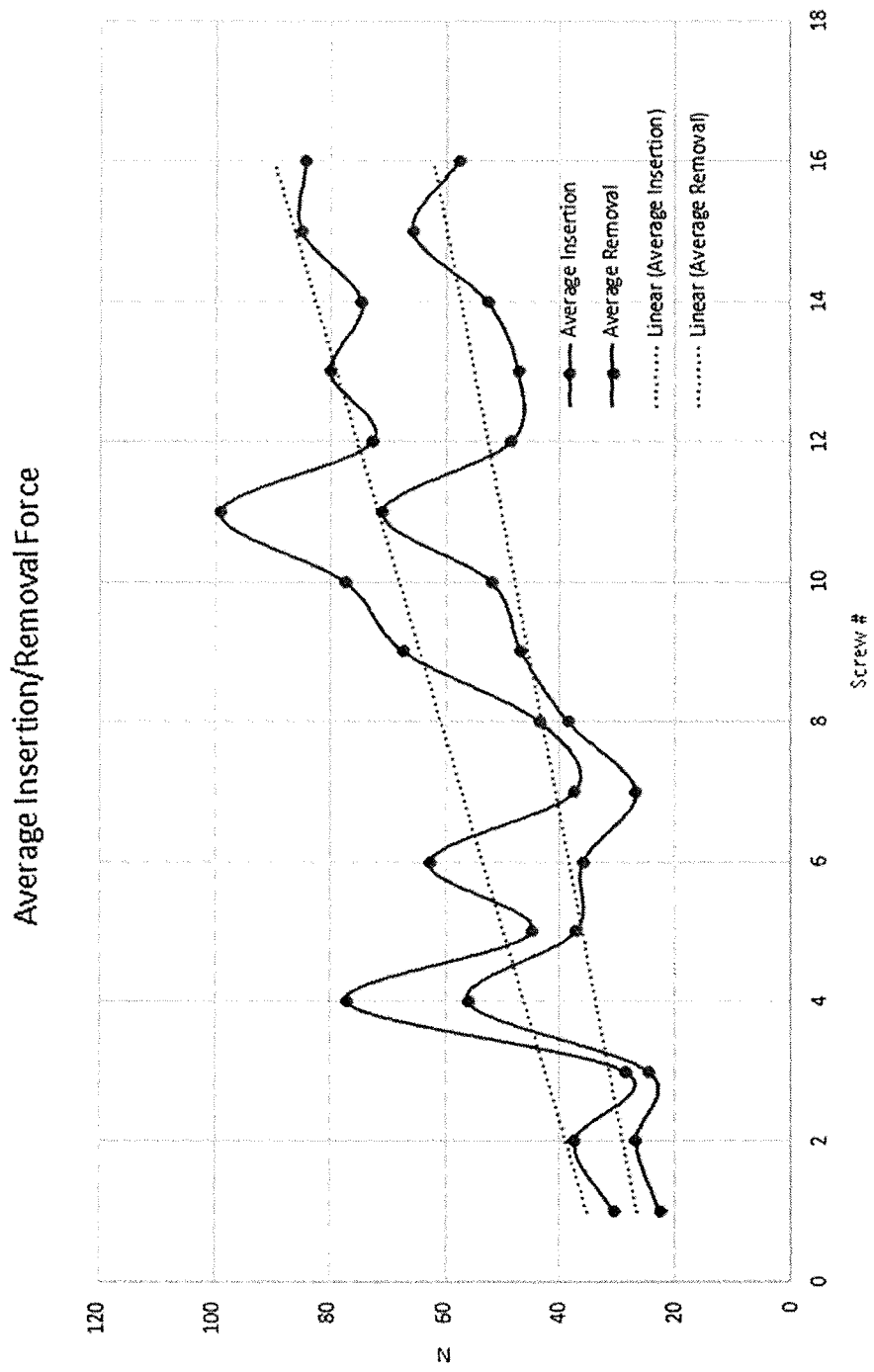

In some aspects, it is necessary or desirable to remove the screw 72 and collar 82 from the aperture 44, 144, and 244. For example, if during the implantation surgery, the practitioner misaligned the implant 1, 1a, 101, 201 and needs to re-adjust its position, the practitioner may need to back the screw 72 out from bone and the aperture 44, 144, and 244, although the aperture 44, 144, and 244 and collar 82 are configured to prevent such a removal of the screw 72. Thus, the implant 1, 1a, 101, and 201 may include one or more structural features to facilitate the ability to remove the screw 72 and collar 82 from the aperture 44, 144, and 244, and pass back out through the opening 45, 145, and 245. In some aspects, it is preferred that the insertion force (insertion of the screw 72 and fixation collar 82 assembly into the aperture 44, 144, and 244,) is less than the removal force (e.g., the force required to remove the screw 72 and collar 82 from the aperture 44, 144, and 244). See, for example, FIG. 22.

Figure 11:
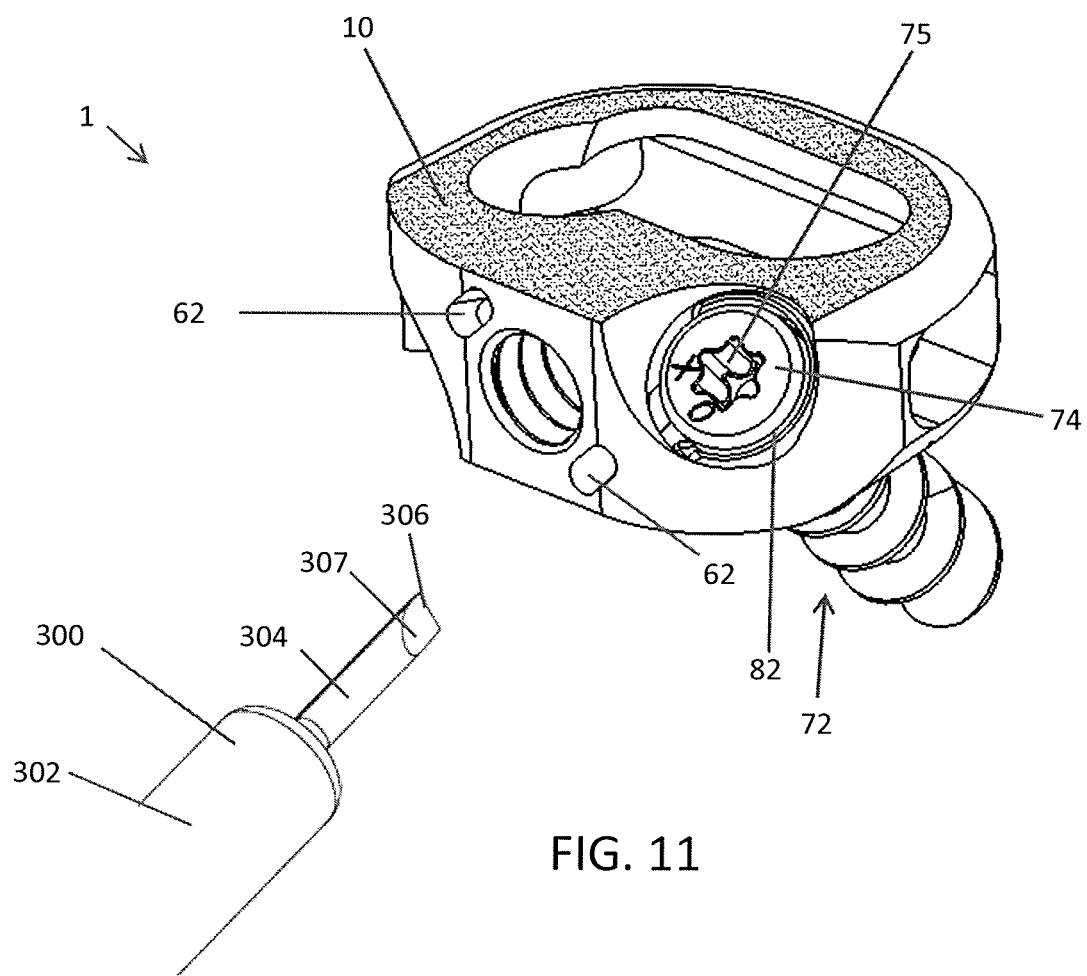
FIG. 11 shows an implant including screw removal slots, and a screw removal tool.
Figure 12A:
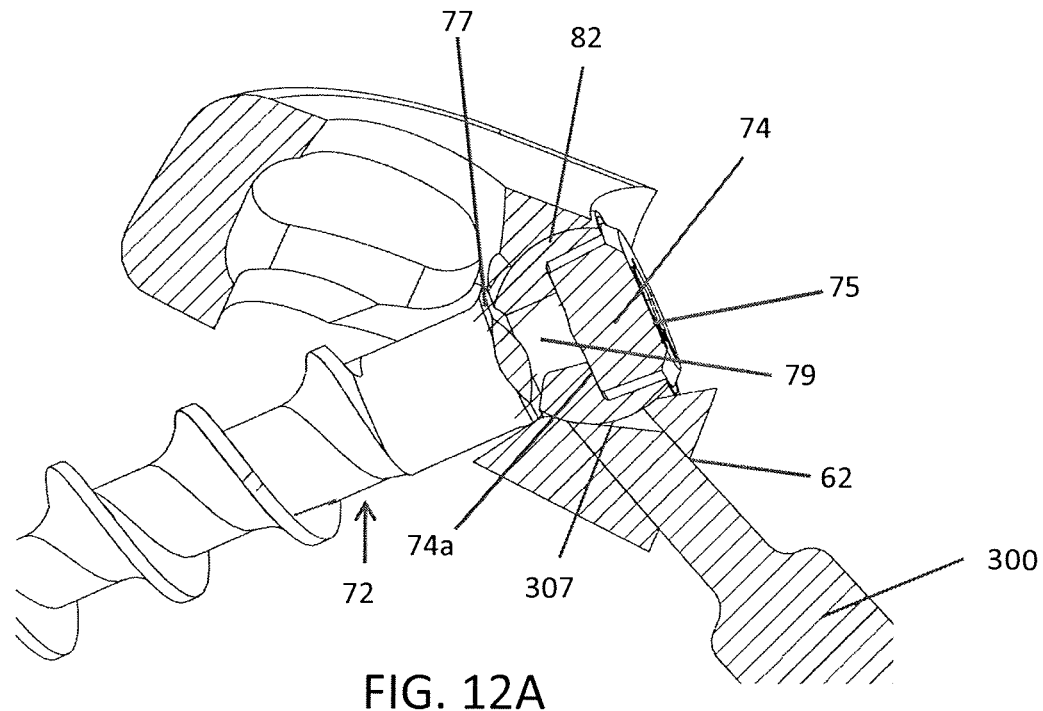
FIGS. 12A and 12B show cross-sectional representations showing the functionality of the screw removal tool.
Figure 12B:
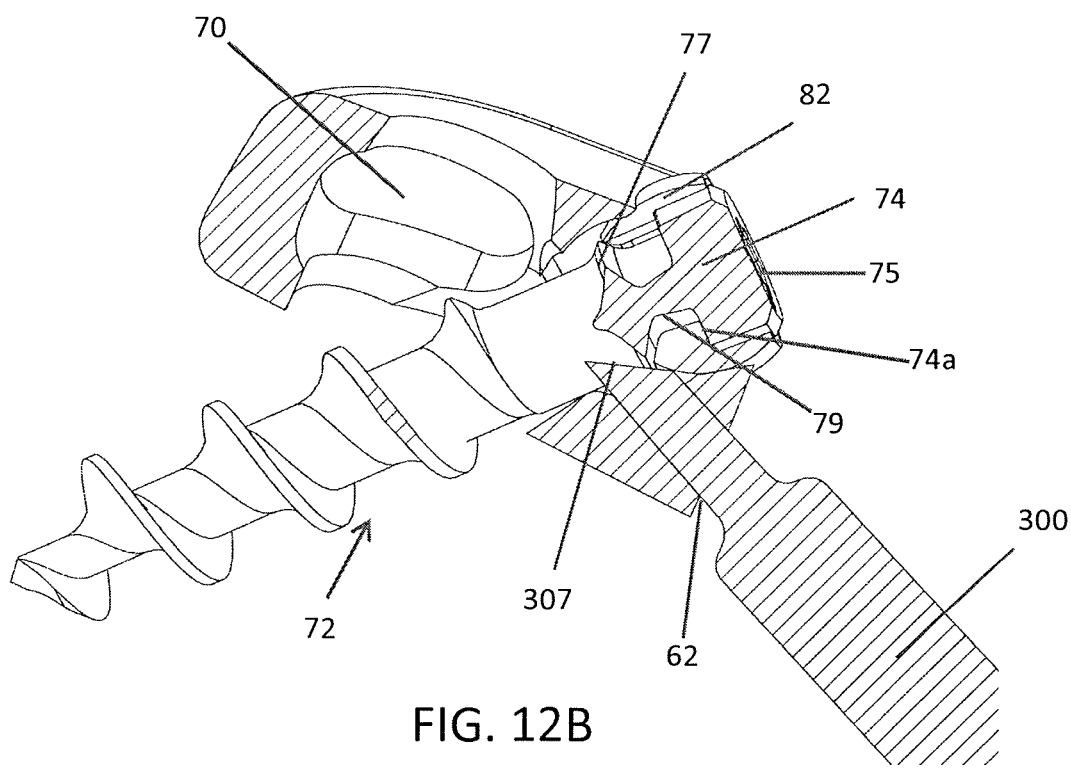

In some aspects, a screw 72 removal feature may comprise one or more slots 62 proximal to the aperture 44, 144, and 244, which pass through the body of the implant 1, 1a, 101, and 201 and into the aperture 44, 144, and 244 (the one or more slots 62 are thus in communication with the one or more apertures 44, 144, and 244). The one or more slots 62 may originate on the anterior 40, 140, 240 portion (FIGS. 10A, 10B, and 11), the posterior portion 50, 150, 250 (not shown), or one or more of the sidewalls 30, 130, and 230 (not shown). A tool 300 may be inserted into the one or more slots 62, contacted with the fixation collar 82, and maneuvered to dislodge the fixation collar 82 from the aperture 44, 144, and 244 (FIGS. 11, 12A, and 12B). Optionally, the outer surface 81 of the collar 82 sidewall 85 may comprise one or more slots that may be engaged by the end of the tool 300 in order to enhance the ability to dislodge the fixation collar 82 out of the aperture 44, 144, and 244 and back through the opening 45, 145, and 245.

Figure 21A:
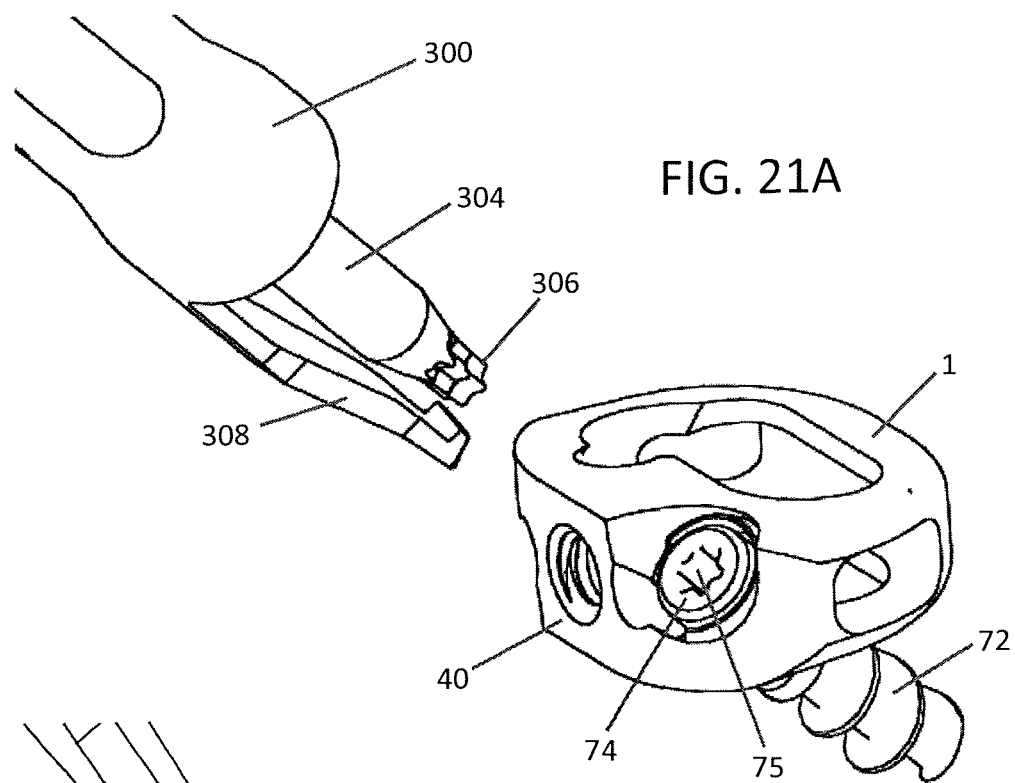
FIG. 21A shows an example of a screw removal tool and implant assembled with a screw.
Figure 21B:
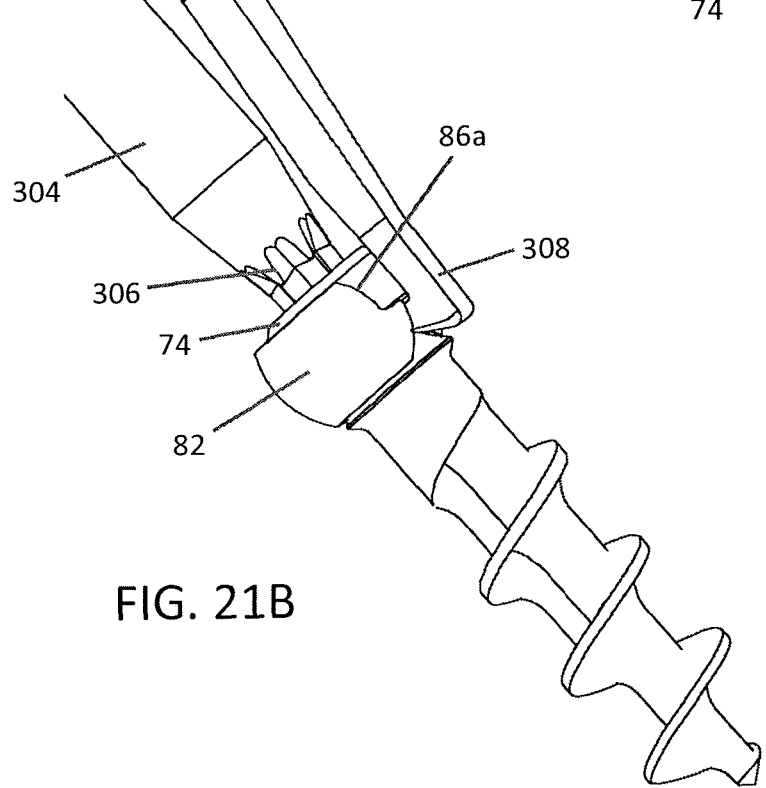
FIG. 21B shows a close-up of the engagement of a screw removal tool and the screw head and, FIG. 22 shows the average insertion and removal force (Newtons) required to insert or remove a screw and collar assembly into or out from an implant aperture. The top solid line shows the average removal force and the top dotted line shows the linear average of the removal force. The bottom solid line shows the average insertion force and the bottom dotted line shows the linear average of the insertion force.

As shown in FIG. 11, FIG. 21A, and FIG. 21B, the screw removal tool 300 may include a handle 302, a shaft 304, and a tip 306. The tip 306 of the screw removal tool 300 may be in the shape of a wedge 307, for example, or a star. The shape is not critical. The tool 300 may also include a clamp 308 to grip one or more of the screw 72 or collar 82.

Figure 14A:
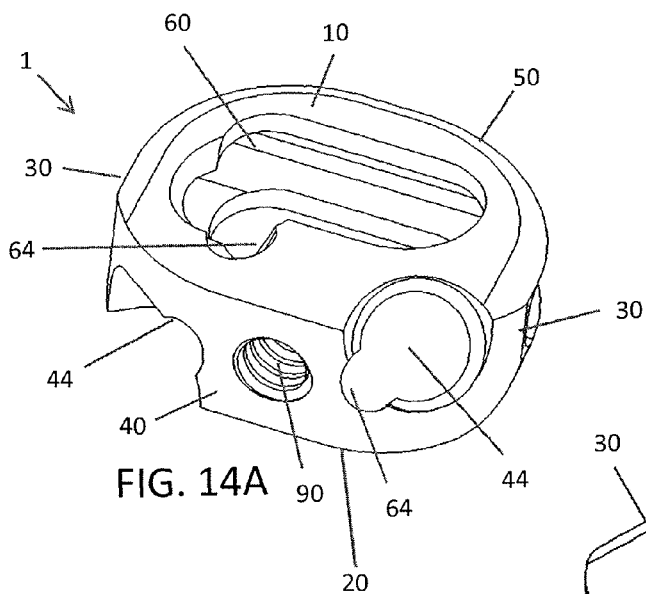
FIG. 14A shows a perspective of an implant including screw removal cutouts.
Figure 14B:
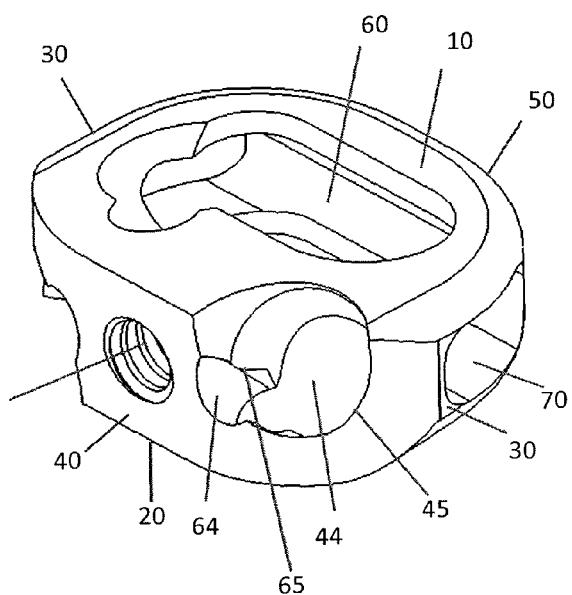
FIG. 14B shows another perspective of an implant including screw removal cutouts.
Figure 14C:
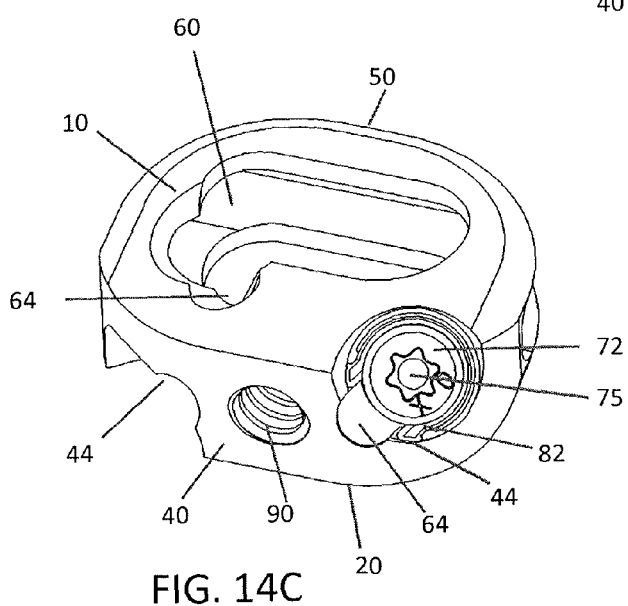
FIG. 14C shows another perspective of an implant including screw removal cutouts and a screw and fixation collar.

In some aspects, a screw 72 removal feature may comprise one or more flutings 64 positioned along the periphery of the aperture 44, 144, and 244 (FIGS. 14A-14C). The one or more flutings 64 pass through the body of the implant 1, 1a, 101, and 201 and into the aperture 44, 144, and 244. A tool 300 may be inserted into the one or more flutings 64, contacted with the fixation collar 82, and maneuvered to dislodge the fixation collar 82 out of the aperture 44, 144, and 244 and back through the opening 45, 145, and 245.

Where the one or more flutings 64 intersect the one or more apertures 44, 144, and 244, an edge 65 exists. This edge 65 may inadvertently snag the ends 84a, 84bs of the notches 86a, 86b. Since such snagging is undesirable, the radiused shape of the notches 86a, 86b minimizes and substantially eliminates such snagging, allowing the collar 82 to freely rotate about the aperture 44, 144, and 244 without catching an edge 65.

The roughened surface topography 80, 180, and 280 helps to facilitate osteointegration (e.g., formation of a direct structural and functional interface between the artificial implant and living bone or soft tissue) with the surrounding living bone. Thus, implant fixation may depend, at least in part, on the stimulation and proliferation of bone modeling and forming cells, such as osteoclasts and osteoblasts and like-functioning cells upon the implant surface. It is believed that these cells attach more readily to relatively rough surfaces rather than smooth surfaces. In this manner, a surface may be bioactive due to its ability to stimulate cellular attachment and osteointegration.

The roughened surface topography 80, 180, and 280 may be on surfaces of the implant 1, 1a, 101, and 201, as well as surfaces of the screw 72 that contact bone. For example, at least a portion of the main shaft 72 below the shoulder 77, as well as the threads 78 may comprise roughened surface topography 80, 180, and 280.

The roughened surface topography 80, 180, and 280 may be comprised of macro features, micro features, and nano features. For example, the roughened surface topography 80, 180, and 280 may be obtained by combining separate macro processing, micro processing, and nano processing steps. Macro features include dimensions measured in millimeters (mm). Micro features comprise dimensions measured in microns (µm). Nano features include dimensions measured in nanometers (nm).

The shapes of the frictional surface protrusions of the roughened surface topography 80, 180, and 280 may be formed using processes and methods commonly applied to remove metal during fabrication of implantable devices such as chemical, electrical, electrochemical, plasma, or laser etching; cutting and removal processes; casting; forging; machining; drilling; grinding; shot peening; abrasive media blasting (such as sand or grit blasting); and combinations of these subtractive processes. Additive processes such as welding, thermal, coatings, sputtering, and optical melt additive processes are also suitable. The resulting surfaces either can be random in the shape and location of the features or can have repeating patterns. This flexibility allows for the design and production of surfaces that resist motion induced by loading in specific directions that are beneficial to the installation process and resist the opposing forces that can be the result of biologic or patient activities such as standing, bending, or turning or as a result of other activities. The shapes of the surface features when overlapping increase the surface contact area but do not result in undercuts that generate a cutting or aggressively abrasive action on the contacting bone surfaces. Regular and repeating patterns are preferred.

These designed surfaces are composed of various sizes of features that, at the microscopic level, interact with the tissues and stimulate their natural remodeling and growth. At a larger scale these features perform the function of generating non-stressful friction that, when combined with a surgical technique that retains the most rigid cortical bone structures in the disc space, allow for a friction fit that does not abrade, chip, perforate, or compromise the critical endplate structures. The overlapping of the three feature sizes can be achieved using manufacturing processes that are completed sequentially and, therefore, do not remove or degrade the previous method.

The first step in the process may be mechanical (e.g., machining though conventional processes) or chemical bulk removal, for example, to generate macro features. The macro features may be of any suitable shape, for example, roughly spherical in shape, without undercuts or protruding tooth-like edges. Other shapes are possible, such as ovals, polygons (including rectangles), cones, triangles, and other shapes. These features may be at least partially overlapped with the next scale (micro) of features using either chemical or mechanical methods (e.g., $AlO_2$ blasting) in predetermined patterns which also do not result in undercuts or protruding sharp edges. The third and final process step is completed through more mild (less aggressive) etching (e.g., HCl acid etching) that, when completed, generates surface features in both the micro and nano scales over both of the features generated by the two previous steps. The nano layer dictates the final chemistry of the implant material.

Figure 15:
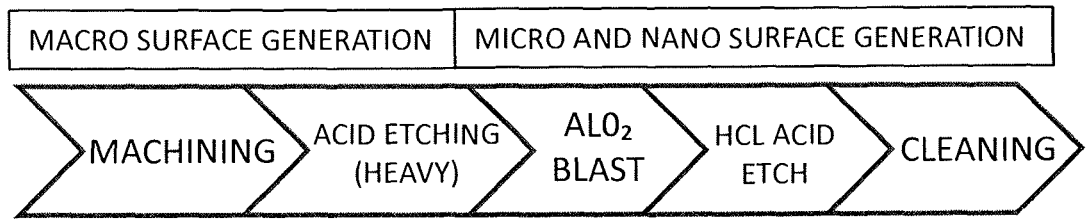
FIG. 15 illustrates process steps that can be used to form macro-, micro-, or nano-scale surface features and structures.

FIG. 15 illustrates one set of process steps that can be used to form the roughened surface topography 80, 180, and 280. First, the part (e.g., screw 72 or implant 1, 1a, 101, and 201) is machined, for example, from a bar stock comprising titanium, and a rough clean may be provided to remove any contaminants from machining. Second, the part may undergo a heavy acid etching (e.g., masked etching). Next, the part may undergo an abrasive blast, for example, using an alumina abrasive. The part may also undergo another acid etch, for example, with a solution comprising hydrochloric acid. Finally, the part may undergo a cleaning (e.g., with water and optionally a detergent). As illustrated, there may be some overlap in the processes that can be applied to form each of the three types of features (macro, micro, and nano). For example, acid etching can be used to form the macro features, then the same or a different acid etching process can be used to form the micro features.

The macro features of the roughened surface topography 80, 180, and 280 are relatively large features (e.g., on the order of millimeters). The macro features may be formed from subtractive techniques (e.g., mechanical or chemical bulk removal, for example) or additive techniques (e.g., deposition). Preferably, the macro features are formed by subtractive techniques, which remove portions of the surface (e.g., from the base material that was used to form the implant 1, 1a, 101, and 201 or screw 72). Suitable subtractive techniques may include, for example, machining (e.g., machine tools, such as saws, lathes, milling machines, and drill presses, are used with a sharp cutting tool to physically remove material to achieve a desired geometry) or masked etching (e.g., portions of the surface are protected by a masking material which resists etching and an etching substance is applied to unmasked portions). The patterns may be organized in regular repeating patterns, and optionally overlap each other. In a preferred embodiment, the macro features may be formed in three, sequential steps.

The macro features may be produced by a heavy masked etching process, for example. Before etching, the surface may be cleaned and optionally blasted with an abrasive (e.g., alumina) in the areas to be chemically textured. Certain areas may be masked in a pattern. The surface may then be chemically milled, for example, using a composition comprising hydrofluoric acid. The maskant and chemical milling may be repeated any number of times necessary to produce the desired pattern and etching depth. After the final etching process, the maskant may be removed and the part may be cleaned. The surface may also be passivated, for example, using an aqueous solution comprising nitric acid. The part may be cleaned and rinsed with water.

The macro features may be formed, for example, using three cut patterns. Specifically, a first cut pattern of the macro features may be formed. The "cut 1" features of the first cut pattern may cover about 20% of the total area of the surface, for example, leaving about 80% of the original surface remaining. The range of these percentages may be about ±20%, preferably ±10%, and more preferably about ±5%. The "cut 1" features of the first cut pattern do not have any undercuts. In one embodiment, these "cut 1" features have the smallest diameter and greatest depth of the macro features that are formed during the sequential steps.

A second cut pattern of the macro features may be formed in the surface. Together, the "cut 1" features of the first cut pattern and the "cut 2" features of the second cut pattern may cover about 85% of the total area of the surface, for example, leaving about 15% of the original surface remaining. The range of these percentages may be about ±10% and preferably ±5%. In an embodiment of the invention, these "cut 2" features have both a diameter and a depth between those of the "cut 1" and "cut 3" features of the macro features that are formed during the first and third steps of the process of forming the macro features of the roughened surface topography 80, 180, and 280.

A third cut pattern of the macro features may be formed in the surface. Together, the "cut 1" features of the first cut pattern, the "cut 2" features of the second cut pattern, and the "cut 3" features of the third cut pattern may cover about 95% of the total area of the surface, for example, leaving about 5% of the original surface remaining. The range of these percentages may be about ±1%. In an embodiment of the invention, these "cut 3" features may have the largest diameter and least depth of the macro features that are formed during the sequential process steps.

After the macro features are formed, additional process steps may be sequentially applied, in turn, to form the micro surface features (e.g., on the order of micrometers) of the roughened surface topography 80, 180, and 280. The micro features may also be formed from subtractive techniques (e.g., mechanical or chemical bulk removal, for example) or additive techniques (e.g., deposition). Preferably, the micro features are also formed by subtractive techniques.

In an exemplary embodiment, the micro features are removed by masked or unmasked etching, such as acid etching. For example, portions of the surface, including portions of the surface exposed by the macro step(s) described above, may be exposed to abrasive blasting, chemical etching, or both. In an exemplary embodiment, the micro process includes an acid etching, with a strong acid, such as hydrochloric acid (HCl), hydroiodic acid (HI), hydrobromic acid (HBr), hydrofluoric (HF), perchloric acid ($HClO_4$), nitric acid ($HNO_3$), and sulfuric acid ($H_2SO_4$). Preferably, the acid etching uses an aqueous solution comprising hydrochloric acid. The etching process may be repeated a number of times as necessitated by the amount and nature of the irregularities required for any particular application. Control of the strength of the etchant material, the temperature at which the etching process takes place, and the time allotted for the etching process allows fine control over the resulting surface produced by the process. The number of repetitions of the etching process can also be used to control the surface features.

By way of example, an etchant mixture of at least one of nitric acid and hydrofluoric acid may be repeatedly applied to a titanium surface to produce an average etch depth of about 0.53 mm. In another example, chemical modification of titanium can be achieved using at least one of hydrofluoric acid, hydrochloric acid, and sulfuric acid. In a dual acid etching process, for example, the first exposure is to hydrofluoric acid and the second is to a hydrochloric acid and sulfuric acid mixture. Chemical acid etching alone may enhance osteointegration without adding particulate matter (e.g., hydroxyapatite) or embedding surface contaminants (e.g., grit particles).

In one embodiment, the micro features are created by abrasive or grit blasting, for example, by applying a stream of abrasive material (such as alumina and sand) to the surface. In an exemplary embodiment, the micro features are created, at least partially, with an aqueous hydrochloric acid etching step and at least partially with an AlO₂ blasting step. Patterns may be organized in regular repeating patterns and optionally overlap each other. After the micro features are formed, it is possible that less than about 3% of the original surface remains. The range of that percentage may be about ±1%.

After the macro features and micro features are formed, additional process steps may be sequentially applied, in turn, to form the nano surface features (e.g., on the order of nanometers) of the roughened surface topography 80, 180, and 280. The nano features may also be formed from subtractive techniques (e.g., mechanical or chemical bulk removal, for example) or additive techniques (e.g., deposition). Preferably, the nano features are also formed by subtractive techniques.

In an exemplary embodiment, the nano features are removed by masked or unmasked etching. For example, portions of the surface, including portions of the surface exposed by the macro and micro steps described above, may be exposed to a chemical etching. In an exemplary embodiment, the nano process also includes an acid etching, with a strong or weak acid, such as hydrochloric acid (HCl), hydroiodic acid (HI), hydrobromic acid (HBr), hydrofluoric (HF), perchloric acid (HClO₄), nitric acid (HNO₃), and sulfuric acid (H₂SO₄). The acid etching process for the nano step is preferably less aggressive than the acid etching process in the macro or micro steps. In other words, a less acidic, mild, or more diluted acid may be selected. In an exemplary embodiment, the nano features are created, at least partially, with an aqueous hydrochloric acid etching step.

As an example, the nano features (or micro features) may be formed by preparing an acid solution comprising hydrochloric acid, water, and titanium; applying the acid solution to the surface; removing the acid solution by rinsing with water; and heating and subsequently cooling the surface.

The acid solution may be prepared using any suitable techniques known in the art. For example, the acid solution may be prepared by combining hydrochloric acid and water, simultaneously or sequentially. The aqueous hydrochloric acid solution may optionally be heated, for example, to a temperature of about 150-250° F. (66-121° C.), preferably about 200-210° F. (93-99° C.), and most preferably about 205° F. (96° C.). The titanium may be seeded (e.g., added) in the aqueous hydrochloric acid solution or may already be present from titanium previously removed from at least one surface of the implant, for example, in a continuous manufacturing process. The solution may optionally be cooled. The acid solution may comprise a concentration of 20-40% hydrochloric acid, preferably about 25-31% hydrochloric acid, and more preferably about 28% hydrochloric acid, based on the total weight of the solution.

It is contemplated that the nano features may also be created by the abrasive or grit blasting, for example, described for the micro processing step. Patterns may be organized in regular repeating patterns and optionally overlap each other. The nano features may also be achieved by tumble finishing (e.g., tumbling). The tumbling process may be wet (e.g., with a lubricant) or dry. After the nano features are formed, it is possible that less than about 1% of the original surface remains.

Any or each of the steps, including the macro, micro, or nano processing steps, may be accompanied by a cleaning step. In addition, the part may be cleaned once the processing steps are complete. For example, the part may be washed in an aqueous environment under agitation and heat with or without a detergent. Following washing, the part may be dried, for example with hot air, heating in a dry oven, or both.

The process steps described in this document can be adjusted to create a mixture of depths, diameters, feature sizes, and other geometries suitable for a particular implant application. The orientation of the pattern of features can also be adjusted. Such flexibility is desirable, especially because the ultimate pattern of the roughened surface topography 80, 180, and 280 of the implant 1, 1a, 101, and 201 should be oriented in opposition to the biologic forces on the implant 1, 1a, 101, and 201 and to the insertion direction.

Several separate parameters can be used to characterize the surface roughness. Among those parameters are the average amplitude, Ra; the maximum peak-to-valley height, Rmax; and the mean spacing, Sm. Surface roughness may be measured using a laser profilometer or other standard instrumentation.

In addition to the parameters Ra, Rmax, and Sm mentioned above, at least two other parameters can be used to characterize the roughness of an implant surface. In summary, the five parameters are: (1) average amplitude, Ra; (2) average peak-to-valley roughness, Rz; (3) maximum peak-to-valley height, Rmax; (4) total peak-to-valley of waviness profile, Wt; and (5) mean spacing, Sm.

Figure 16:
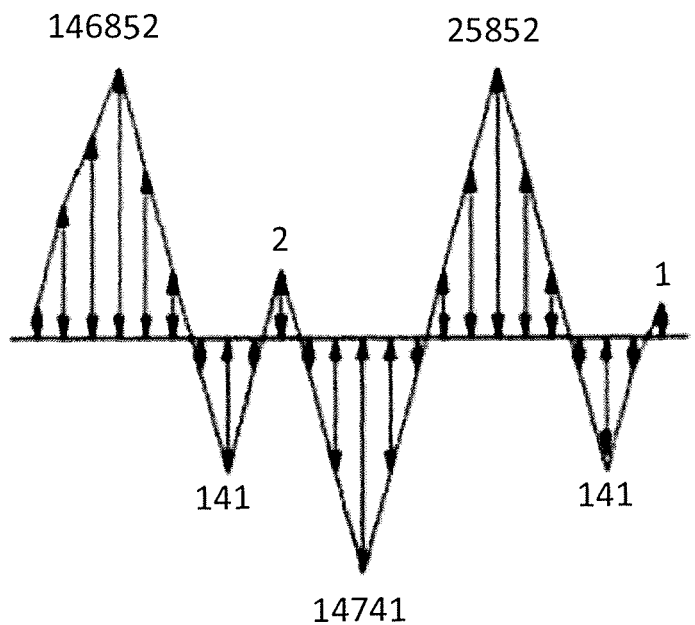
FIG. 16 graphically represents the average amplitude, Ra, of macro-, micro-, or nano-scale surface features and structures.

Average Amplitude Ra. Ra comprises an arithmetic average height. Mathematically, Ra may be computed as the average distance between each roughness profile point and the mean line. In FIG. 16, the average amplitude is the average length of the arrows.

In mathematical terms, this process can be represented by the following Formula I:

$$Ra = \frac{1}{n}\sum_{i=1}^{n} |y_i|$$

Figure 17:
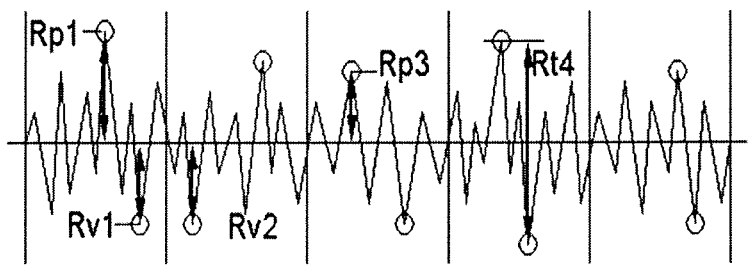
FIG. 17 graphically represents the average peak-to-valley roughness, Rz, of macro-, micro-, or nano-scale surface features and structures.

Average Peak-to-Valley Roughness Rz. The average peak-to-valley roughness, Rz, is defined by the ISO and ASME 1995 and later. Rz is based on one peak and one valley per sampling length. The RzDIN value is based on the determination of the peak-to-valley distance in each sampling length. These individual peak-to-valley distances are averaged, resulting in the RzDIN value, as illustrated in FIG. 17.

Figure 18:
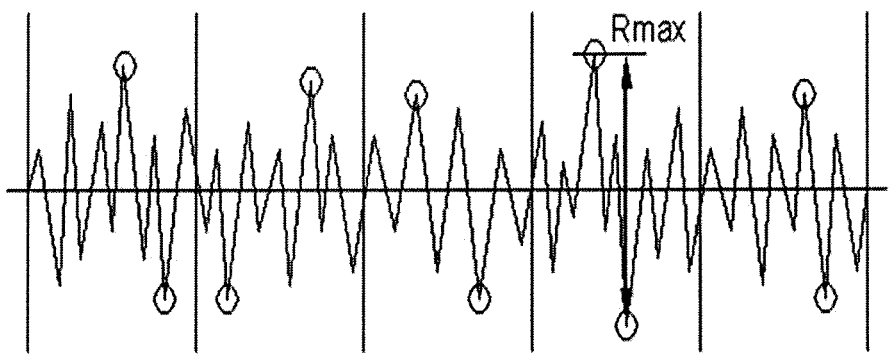
FIG. 18 graphically represents the maximum peak-to-valley height, Rmax, of macro-, micro-, or nano-scale surface features and structures.

Maximum Peak-to-Valley Height Rmax. The maximum peak-to-valley height, Rmax, comprises the maximum peak-to-valley distance in a single sampling length—as illustrated in FIG. 18.

Figure 19:
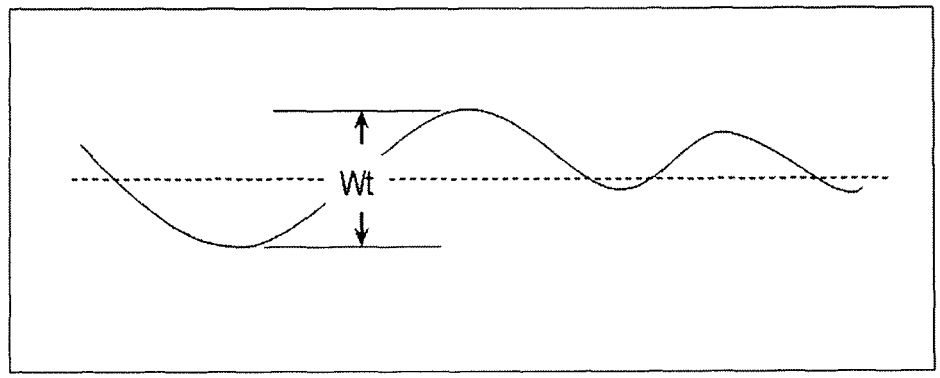
FIG. 19 graphically represents the total peak-to-valley of waviness of profile macro-, micro-, or nano-scale surface features and structure.

Total Peak-to-Valley of Waviness Profile Wt. The total peak-to-valley of waviness profile (over the entire assessment length) is illustrated in FIG. 19.

Figure 20:
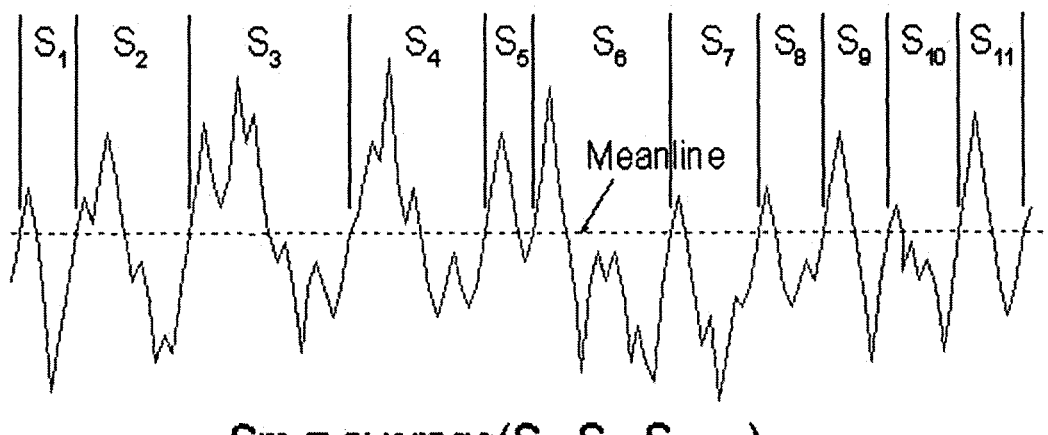
FIG. 20 graphically represents the mean spacing, Sm, of macro-, micro-, or nano-scale surface features and structures.

Mean Spacing Sm. The mean spacing, Sm, comprises the average spacing between positive mean line crossings. The distance between each positive (upward) mean line crossing is determined and the average value is calculated, as illustrated in FIG. 20.

The parameters Sm, Rmax, and Ra can be used define the surface roughness following formation of each of the three types of features macro, micro, and nano. Such data are provided in Tables 1-3.

TABLE 1

Surface Feature Size and Roughness (Metric): Macro (μm)

| | Size (Sm) | Depth (Rmax) | Roughness (Ra) |
|---|---|---|---|
| Max. | 2,000 | 500 | 200 |
| Min. | 400 | 40 | 20 |
| Avg. | 1,200 | 270 | 110 |

TABLE 2

Surface Feature Size and Roughness (Metric): Micro (μm)

| | Size (Sm) | Depth (Rmax) | Roughness (Ra) |
|---|---|---|---|
| Max. | 400 | 40 | 20 |
| Min. | 20 | 2 | 1 |
| Avg. | 210 | 11 | 5.5 |

TABLE 3

Surface Feature Size and Roughness (Metric): Nano (μm)

| | Size (Sm) | Depth (Rmax) | Roughness (Ra) |
|---|---|---|---|
| Max. | 20 | 2 | 1 |
| Min. | 0.5 | 0.2 | 0.01 |
| Avg. | 10.25 | 1.1 | 0.505 |

The macro features for each of the three parameters may comprise the following preferred ranges (all measurements in microns). In some aspects, the macro mean spacing, Sm, is about 400 to about 2000 micrometers. More preferably, the macro mean spacing is about 750 to about 1750 micrometers, and more preferably, the macro mean spacing is about 1000 to about 1500 micrometers. In some aspects, the macro mean spacing is about 500 to about 1000 micrometers, about 600 to about 900 micrometers, about 700 to about 1000 micrometers, about 750 to about 1200 micrometers, about 800 to about 1300 micrometers, about 900 to about 1300 micrometers, about 1000 to about 1300 micrometers, about 1100 to about 1300 micrometers, about 1100 to about 1400 micrometers, about 1150 to about 1250 micrometers, about 1150 to about 1350 micrometers, about 1200 to about 1500 micrometers, or about 1200 to about 1400 micrometers. In some aspects, the macro peak-to-valley height, Rmax, is about 40 to about 500 micrometers. More preferably, the macro peak-to-valley height is about 150 to about 400 micrometers, and more preferably, about 250 to about 300 micrometers. In some aspects, the macro mean peak-to valley height is about 100 to about 450 micrometers, about 200 to about 400 micrometers, about 200 to about 300 micrometers, about 260 to about 280 micrometers, about 250 to about 350 micrometers, about 260 to about 320 micrometers, or about 270 to about 300 micrometers. In some aspects, the macro average amplitude, Ra, is about 20 to about 200 micrometers. More preferably, the macro average amplitude is about 50 to about 150 micrometers, and more preferably about 100 to about 120 micrometers. In some aspects, the macro average amplitude is about 80 to about 180 micrometers, about 90 to about 160 micrometers, about 90 to about 140 micrometers, about 100 to about 150 micrometers, about 100 to about 130 micrometers, about 105 to about 125 micrometers, or about 105 to about 115 micrometers.

The micro features for each of the three parameters may comprise the following preferred ranges (all measurements in microns). In some aspects, the micro mean spacing, Sm, is about 20 to about 400 micrometers. More preferably, the micro mean spacing is about 100 to about 300 micrometers, and more preferably, the macro mean spacing is about 200 to about 220 micrometers. In some aspects, the micro mean spacing is about 50 to about 350 micrometers, about 75 to about 350 micrometers, about 75 to about 300 micrometers, about 100 to about 325 micrometers, about 100 to about 250 micrometers, about 120 to about 220 micrometers, about 150 to about 250 micrometers, about 180 to about 240 micrometers, about 190 to about 230 micrometers, or about 205 to about 215 micrometers. In some aspects, the micro peak-to-valley height, Rmax, is about 2 to about 40 micrometers. More preferably, the micro peak-to-valley height is about 5 to about 25 micrometers, and more preferably, about 6 to about 16 micrometers. In some aspects, the micro mean peak-to valley height is about 0.5 to about 50 micrometers, about 1 to about 45 micrometers, about 1 to about 40 micrometers, about 1 to about 30 micrometers, about 1 to about 20 micrometers, about 1 to about 15 micrometers, about 2 to about 50 micrometers, about 2 to about 30 micrometers, about 2 to about 25 micrometers, about 3 to about 40 micrometers, about 3 to about 30 micrometers, about 4 to about 40 micrometers, about 4 to about 30 micrometers, about 5 to about 40 micrometers, about 5 to about 30 micrometers, about 7 to about 20 micrometers, about 7 to about 15 micrometers, about 8 to about 14 micrometers, or about 9 to about 13 micrometers. In some aspects, the micro average amplitude, Ra, is about 1 to about 20 micrometers. More preferably, the micro average amplitude is about 1 to about 10 micrometers, and more preferably about 3 to about 7 micrometers. In some aspects, the micro average amplitude is about 0.5 to about 30 micrometers, about 0.5 to about 25 micrometers, about 1 to about 15 micrometers, about 1 to about 10 micrometers, about 1 to about 9 micrometers, about 1 to about 7 micrometers, about 2 to about 9 micrometers, or about 4 to about 7 micrometers.

The nano features for each of the three parameters may comprise the following preferred ranges (all measurements in microns). In some aspects, the nano mean spacing, Sm, is about 0.5 to about 20 micrometers. More preferably, the nano mean spacing is about 5 to about 15 micrometers, and more preferably, the macro mean spacing is about 8 to about 12 micrometers. In some aspects, the nano mean spacing is about 0.1 to about 30 micrometers, about 0.25 to about 25 micrometers, about 0.5 to about 15 micrometers, about 0.5 to about 13 micrometers, about 1 to about 250 micrometers, about 1 to about 20 micrometers, about 1 to about 150 micrometers, about 2 to about 18 micrometers, about 2 to about 12 micrometers, about 7 to about 14 micrometers, or about 9 to about 11.5 micrometers. In some aspects, the nan peak-to-valley height, Rmax, is about 0.2 to about 2 micrometers. More preferably, the nano peak-to-valley height is about 0.5 to about 1.5 micrometers, and more preferably, about 0.8 to about 1.4 micrometers. In some aspects, the nano mean peak-to valley height is about 0.05 to about 5 micrometers, about 0.1 to about 3 micrometers, about 0.1 to about 2 micrometers, about 0.1 to about 1.5 micrometers, about 0.1 to about 0.4 micrometers, about 0.2 to about 3 micrometers, about 0.2 to about 2.5 micrometers, about 0.2 to about 1.8 micrometers, about 0.6 to about 1.6 micrometers, about 0.7 to about 1.5 micrometers, or about 0.9 to about 1.3 micrometers. In some aspects, the nano average amplitude, Ra, is about 0.01 to about 1 micrometers. More preferably, the nano average amplitude is about 0.05 to about 0.75 micrometers, and more preferably about 0.3 to about 0.7 micrometers. In some aspects, the nano average amplitude is about 0.005 to about 2 micrometers, about 0.005 to about 1.5 micrometers, about 0.01 to about 0.75 micrometers, about 0.01 to about 1.1 micrometers, about 0.01 to about 0.9 micrometers, about 0.01 to about 0.07 micrometers, about 0.025 to about 0.75 micrometers, or about 0.04 to about 0.6 micrometers.

The invention is not limited to the embodiments described and exemplified above, but is capable of variation and modification within the scope of the appended claims.

What is claimed:

1. A screw and collar assembly comprising:
   a screw comprising a head, a shoulder beneath the head, a groove between the head and shoulder, and a threaded shaft beneath the shoulder; and
   a C-shaped fixation collar comprising a sidewall at least partially surrounding a void that is substantially in the center of the collar and extends along an axis that is parallel to the vertical axis of the fixation collar, the sidewall comprising a recessed top portion that forms a ridge on which the bottom of the head sits when the screw is inside of the void, a bottom portion that engages the groove when the screw is inside of the void, end regions that are partially flexible along an axis that is perpendicular to the vertical axis of the fixation collar, and a first end and second end defining a gap in communication with the void, each end comprising a first notch above the ridge and a second notch below the ridge;
   wherein the gap has a width slightly narrower than the inner diameter of the groove, and the void has a diameter narrower than the outer diameter of the shoulder such that the screw may not be moved axially through the fixation collar, at least higher than the shoulder.

2. The screw and collar assembly of claim 1, wherein the sidewall has a convex outer surface configured to engage an aperture having concave sidewalls in an implant in a way that inhibits axial movement of the screw and collar assembly out from the aperture once engaged, but allows limited pivotal and rotational movement of the screw and collar assembly about the aperture.

3. The screw and collar assembly of claim 1, wherein the groove and bottom portion comprise compatibly shaped undercuts.

4. The screw and collar assembly of claim 1, wherein the first notch is radiused in a direction away from the gap.

5. The screw and collar assembly of claim 1, wherein the second notch is radiused in a direction away from the gap.

6. The screw and collar assembly of claim 1, wherein first notch on each end widens the gap above the ridge.

7. The screw and collar assembly of claim 6, wherein the width of the gap above the ridge is about 10% to about 60% greater than the width of the gap below the ridge.

8. The screw and collar assembly of claim 1, wherein first notch on each end defines a ledge on the ridge.

9. The screw and collar assembly of claim 8, wherein the ledge comprises blunt and radiused edges.

10. The screw and collar assembly of claim 1, wherein the void has a diameter narrower than the outer diameter of the screw threads.

11. The screw and collar assembly of claim 1, wherein the fixation collar comprises a plastic, polymeric, or non-metal composite material.

12. The screw and collar assembly of claim 1, wherein the fixation collar comprises a metal.

13. The screw and collar assembly of claim 1, wherein at least the threaded shaft of the screw comprises a roughened surface topography comprising macro-, micro-, and nano-scale structures capable of facilitating bone growth.

14. A system for anchoring an implant to adjacent bone, comprising
   a screw comprising a head, a shoulder beneath the head, a groove between the head and shoulder, and a threaded shaft beneath the shoulder;
   a C-shaped fixation collar comprising a sidewall at least partially surrounding a void that is substantially in the center of the collar and extends along an axis that is parallel to the vertical axis of the fixation collar, the sidewall comprising a convex outer surface, a recessed top portion that forms a ridge on which the bottom of the head sits when the screw is inside of the void, a bottom portion that engages the groove when the screw is inside of the void, end regions that are partially flexible along an axis that is perpendicular to the vertical axis of the fixation collar, and a first end and second end defining a gap in communication with the void, each end comprising a first notch above the ridge and a second notch below the ridge, wherein the gap has a width slightly narrower than the inner diameter of the groove, and the void has a diameter narrower than the outer diameter of the shoulder such that the screw may not be moved axially through the fixation collar, at least higher than the shoulder; and
   an implant comprising one or more apertures extending through the implant and comprising an opening having a diameter narrower than the widest point of the convex outer surface of the fixation collar and a concave inner surface that engages the sidewall of the fixation collar when the fixation collar is inside of the aperture.

15. The system of claim 14, wherein the one or more apertures further comprise one or more flutings along the periphery of the aperture.

16. The system of claim 14, wherein the implant further comprises one or more slots into which a tool may be inserted to dislodge the fixation collar from the aperture.

17. The system of claim 14, wherein the first notch is radiused in a direction away from the gap.

18. The system of claim 14, wherein the fixation collar comprises a plastic, polymeric, ceramic, or non-metal composite material.

19. The system of claim 14, wherein the fixation collar comprises a metal.

20. The system of claim 14, wherein at least the threaded shaft of the screw comprises a roughened surface topography comprising macro-, micro-, and nano-scale structures capable of facilitating bone growth.

21. The system of claim 14, further comprising a screw removal tool.

* * * * *